United States Patent
Gerstner et al.

(10) Patent No.: US 9,895,201 B2
(45) Date of Patent: Feb. 20, 2018

(54) CANTILEVER ORGANIZATIONAL RACK SYSTEM FOR SUPPORTING SURGICAL INSTRUMENTATION

(71) Applicant: Flex Operating Room, LLC, Pittsford, NY (US)

(72) Inventors: Jeffrey Gerstner, Pittsford, NY (US); Gregory Bonisteel, Rochester, NY (US)

(73) Assignee: Flex Operating Room, LLC, Pittsford, NY (US)

( * ) Notice: Subject to any disclaimer, the term of this patent is extended or adjusted under 35 U.S.C. 154(b) by 0 days.

(21) Appl. No.: 15/055,280

(22) Filed: Feb. 26, 2016

(65) Prior Publication Data

US 2016/0249996 A1    Sep. 1, 2016

Related U.S. Application Data

(60) Provisional application No. 62/121,710, filed on Feb. 27, 2015.

(51) Int. Cl.
| | |
|---|---|
| *A47F 7/00* | (2006.01) |
| *A47F 3/14* | (2006.01) |
| *A47F 5/08* | (2006.01) |
| *A61B 50/22* | (2016.01) |
| *F16M 11/42* | (2006.01) |

(Continued)

(52) U.S. Cl.
CPC ............ *A61B 50/22* (2016.02); *A47B 96/027* (2013.01); *A47F 5/0025* (2013.01); *A47F 5/137* (2013.01); *A61B 50/13* (2016.02); *A61B 50/15* (2016.02); *A61B 50/20* (2016.02); *A61B 50/33* (2016.02);

(Continued)

(58) Field of Classification Search
CPC ......... A61B 50/22; A61B 50/13; A61B 50/15; A61B 50/20; A61B 50/33; A61B 50/34; A47F 5/0025; A47F 5/108; A47F 5/103; A47F 5/135; A47F 5/137; A47F 5/10; A47F 5/16; A47F 2005/165; A47F 5/12; F16M 11/42; F16M 11/20; A47B 43/00;
(Continued)

(56) References Cited

U.S. PATENT DOCUMENTS

| | | | | |
|---|---|---|---|---|
| 338,011 A | * | 3/1886 | Adams, Jr. ............. | D06F 57/08 |
| | | | | 211/170 |
| 538,145 A | * | 4/1895 | Allen ..................... | A47B 43/00 |
| | | | | 108/1 |

(Continued)

*Primary Examiner* — Jennifer E. Novosad
(74) *Attorney, Agent, or Firm* — Fish & Richardson P.C.

(57) ABSTRACT

A vertical organizational system for use in the operating room during surgery to hold surgical instrumentation is provided. The system includes a vertical support including a height and angle adjustable portion; vertical support assembly, a back panel, a pivoting spine assembly, a base interface member, casters, a base, an interactive user display, a tray shelf, a receptacle container, a primary working shelf, a formed base, a custom sterile drape, an identification system, a telescoping mayo stand, telescoping step stool, a light assembly, a sterile aerosol assembly, an instrument tray attachment device, telescoping cross rail extensions and a ceiling mounted boom assembly. The cantilever shelves are detachably attachable from the cross rails and helps maintain the sterile state of the instrumentation trays even if the rest of the rack is not maintained in a sterile state.

10 Claims, 33 Drawing Sheets

(51) Int. Cl.
*A47F 5/13* (2006.01)
*A47B 96/02* (2006.01)
*A47F 5/00* (2006.01)
*A61B 50/13* (2016.01)
*A61B 50/15* (2016.01)
*A61B 50/20* (2016.01)
*A61B 50/33* (2016.01)
*A61B 50/34* (2016.01)
*A47F 5/10* (2006.01)

(52) U.S. Cl.
CPC ............. *A61B 50/34* (2016.02); *F16M 11/42* (2013.01); *A47F 5/108* (2013.01)

(58) Field of Classification Search
CPC ..... A47B 83/03; A47B 47/022; A47B 57/045; A47B 57/04; A47B 96/025; A47B 96/027
USPC ......... 211/85.13, 13.1, 130.1, 195, 198, 204, 211/206, 193, 103, 150, 128.1, 133.1, 211/133.3; 280/79.3; 248/129, 128, 133, 248/136, 139, 140; 108/96, 99, 162, 163, 108/164
See application file for complete search history.

(56) References Cited

U.S. PATENT DOCUMENTS

| | | | | |
|---|---|---|---|---|
| 725,625 A * | 4/1903 | Lurye | ............... | A47B 21/0314 108/96 |
| 907,171 A * | 12/1908 | Poles et al. | ............ | A47G 25/12 211/195 |
| 1,104,004 A * | 7/1914 | Rathbone | ................. | A24F 9/14 131/257 |
| 1,204,286 A * | 11/1916 | Lengquist | .......... | A47B 21/0314 108/100 |
| 1,531,540 A | 3/1925 | Calero | .................... | B41J 29/15 211/204 |
| 1,715,163 A * | 5/1929 | Kim | ...................... | A47F 5/0025 211/84 |
| 2,002,128 A * | 5/1935 | Reidenbaugh | ............ | A47F 5/01 108/107 |
| 2,148,548 A * | 2/1939 | Gregory | .................. | A47F 5/108 211/85 |
| 2,530,231 A * | 11/1950 | Detweiler | ............... | A47F 5/108 108/99 |
| 2,707,841 A * | 5/1955 | Figura | ................... | D06F 81/006 211/204 |
| 3,294,266 A * | 12/1966 | Snow | ........................ | B65F 1/12 248/133 |
| 4,109,892 A * | 8/1978 | Hartung | ................. | A47B 97/04 248/449 |
| 4,113,218 A | 9/1978 | Linder | | |
| 5,096,072 A * | 3/1992 | Link | ......................... | A47F 5/13 211/130.1 |
| 5,201,429 A * | 4/1993 | Hikosaka | ............. | B65G 1/1375 211/59.2 |
| 5,289,957 A * | 3/1994 | Huang | ..................... | B60R 7/04 224/275 |
| 5,310,066 A | 5/1994 | Konstant | | |
| 5,454,722 A | 10/1995 | Holland et al. | | |
| 5,590,796 A * | 1/1997 | Herman | .................. | A47F 5/108 108/99 |
| 5,610,811 A | 3/1997 | Honda | | |
| 5,749,480 A * | 5/1998 | Wood | ..................... | A47B 57/04 211/150 |
| 5,927,214 A | 7/1999 | Schwartz et al. | | |
| 5,991,728 A | 11/1999 | DeBusk et al. | | |
| 6,019,102 A | 2/2000 | Becker | | |
| 6,039,228 A * | 3/2000 | Stein | ......................... | B60R 9/06 211/193 |
| 6,105,797 A * | 8/2000 | Haisma | .................... | A47F 5/137 211/130.1 |
| 6,158,437 A | 12/2000 | Vagley | | |
| 6,189,459 B1 | 2/2001 | DeAngelis | | |
| 6,224,072 B1 * | 5/2001 | Weck | ...................... | B62B 3/02 211/204 |
| 6,267,345 B1 * | 7/2001 | Turner | .................... | A47B 97/04 248/129 |
| 6,315,308 B1 * | 11/2001 | Konopka | ............... | A47B 21/00 108/50.02 |
| 6,382,434 B1 * | 5/2002 | Silberg | .................... | A47F 5/137 211/195 |
| 6,497,233 B1 | 12/2002 | DeAngelis | | |
| 6,823,805 B2 | 11/2004 | Becker | | |
| 7,249,680 B2 * | 7/2007 | Wang | ...................... | A47B 57/04 211/150 |
| 7,350,649 B1 * | 4/2008 | Martens | .................. | A47B 57/06 211/150 |
| 7,624,954 B2 * | 12/2009 | Randle, Jr. | ........... | B60N 2/2848 248/129 |
| 7,731,136 B1 * | 6/2010 | Chisolm | ............. | A61M 5/1415 211/204 |
| 7,748,802 B2 * | 7/2010 | Peruzzi | ................ | A47B 46/005 211/195 |
| 7,815,202 B2 * | 10/2010 | Richards | ................ | A47F 5/135 211/126.8 |
| 8,074,815 B2 | 12/2011 | Gerstner | | |
| 8,104,787 B2 * | 1/2012 | Haley | ..................... | B62B 3/108 108/115 |
| 8,323,034 B1 | 12/2012 | Youngblood | | |
| 8,371,592 B2 * | 2/2013 | Feitel | ....................... | B05B 9/007 248/139 |
| 8,464,994 B2 * | 6/2013 | Chiu | ........................ | B25H 1/04 144/286.1 |
| 8,689,704 B2 | 4/2014 | Hodges et al. | | |
| 8,763,824 B2 * | 7/2014 | Alcock | .............. | A47G 25/0664 211/206 |
| 8,911,677 B2 | 12/2014 | Gerstner et al. | | |
| 8,950,344 B2 | 2/2015 | Lewis et al. | | |
| 2002/0023889 A1 * | 2/2002 | Larbaletier | ................ | A47F 5/12 211/150 |
| 2005/0275178 A1 * | 12/2005 | Huesdash | ............ | A47B 57/482 280/47.35 |
| 2008/0073304 A1 * | 3/2008 | Corbett | ................. | B65G 49/062 211/198 |
| 2009/0045154 A1 * | 2/2009 | Gerstner | ................ | A61B 50/20 211/126.15 |
| 2010/0289236 A1 * | 11/2010 | Bennett | ..................... | B62B 3/10 280/79.11 |
| 2012/0006767 A1 * | 1/2012 | Bennett | ................. | A47B 81/00 211/26 |
| 2012/0248047 A1 * | 10/2012 | Tanabe | .................. | A47B 43/00 211/13.1 |
| 2014/0216305 A1 | 8/2014 | Hodges et al. | | |
| 2016/0249996 A1 * | 9/2016 | Gerstner | ............... | A47F 5/0025 211/130.1 |

\* cited by examiner

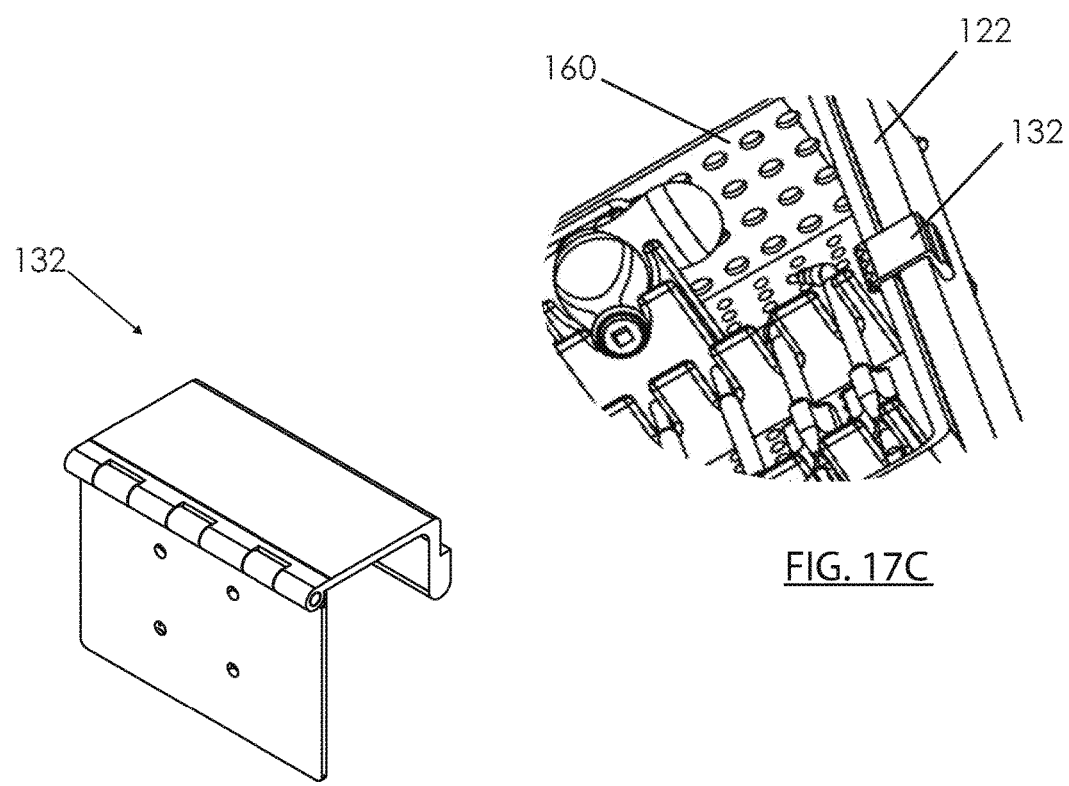
FIG. 17C
FIG. 17B
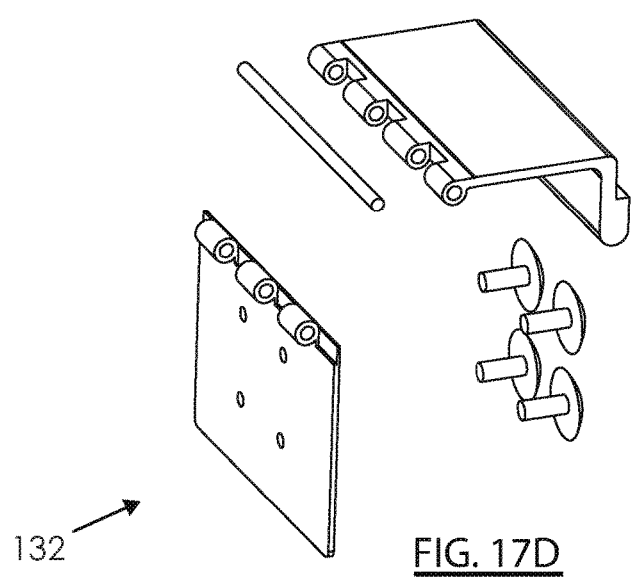
FIG. 17D

CANTILEVER ORGANIZATIONAL RACK SYSTEM FOR SUPPORTING SURGICAL INSTRUMENTATION

This application is a non-provisional which claims the benefit of U.S. provisional patent application 62/121,710 filed Feb. 27, 2015, entitled CANTILEVER ORGANIZATIONAL RACK SYSTEM FOR SUPPORTING SURGICAL INSTRUMENTATION, which is incorporated herein by reference.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

Field of the Invention

The present disclosure relates generally to surgical instrument organization and utilization throughout the life cycle of tools, instruments, and implant devices used in hospitals and surgery centers for a surgical procedure. In particular, the disclosure relates to an organizational system capable of providing a systematic protocol to ensure reliable inventory management for medical applications, more particularly to cabinets, racks, shelving, sterilization enhancement, software for operating rooms to be used during surgery.

Description of Related Art

Various cabinets, racks, tables and shelving have been used for assembling, storing, and transporting medical instruments, tools, and implant devices throughout hospitals and surgery centers for medical operations and procedures. Typically surgical instruments, tools and implant devices are washed, sterilized, wrapped, and stored until required instrumentation is set up in the operating room prior to surgery or a medical procedure.

The numerous personnel including but not limited to patients, hospital administration, surgeons, nursing staff, scrub technicians, sterile processing employees, device manufacturers, manufacturers' representatives along with the vast number of tools and instruments required for a specific surgery creates a need for precise coordination.

SUMMARY OF THE INVENTION

The present disclosure is directed to various designs for an organizational system for use in the operating room during surgery to hold instruments. Preferred features for the design of the present disclosure include the following:

1. multi-level rack design with adjustable angle shelves;
2. modular rack units and options allow for customized room set-up based on surgeon, procedure, instrument requirements, and space limitations;
3. mobility for easy movement of the racks around the hospital and operating room;
4. removable sterilizable shelves that are easily set up, broken down, stored, wrapped and/or handled;
5. rack includes a custom sterile drape;
6. rack allows for co-branding opportunities, such as company and hospital brand, procedure techniques, logos, etc.
7. adjustable rack height for technician or surgeon comfort and/or visual preferences;
8. adjustable spine angle and orientation for technician or surgeon comfort and/or visual preferences;
9. rack collapses into a down position for easy storage and stacking of multiple racks when not in use;
10. rack may be designed to support at least 2 or more full instruments cases per shelf level; and
11. rack ensures a consistent protocol for the use of surgical instruments; and Various embodiments of the present disclosure may exhibit one or more of the following objects, features and/or advantages:

1. reduces or eliminates need for sterile cloth drapes to cover stainless steel tables;
2. helps organize equipment trays with increased visibility and accessibility of instruments inside an operating room;
3. reduces occurrence of situations where instruments are lost or misplaced due to a disorganized and inconsistent surgical room set-up and inventory management;
4. allows accessible and organized surgery room storage of hundreds of instruments;
5. prevents instrument trays from being "stacked" together during long surgical procedures and associated risk of bacteria growth;
6. reduces or eliminates sterile field violations due to lack of floor space in sterile working area;
7. helps reduce hospital infection rate;
8. improved portability, instrument work space, efficiency, safety and/or standardization;
9. helps to reduce the number of personnel in the operating room during surgery;
10. reduces inefficiencies associated with instrumentation and implant use;
11. creates opportunity for better space management of operating rooms;
12. creates a standardized protocol for instrumentation use depending on surgery type, surgeon, device manufacturer; and
13. allows a manufacturer's representative to be more effective and efficient.

According to one aspect of the present disclosure, an organization rack system includes a rack assembly and a detachably attachable shelf unit. The rack assembly includes a frame assembly, telescoping tube assembly and a spine assembly. The frame assembly includes a base, and at least one vertical support rail. The vertical support rail is mechanically connected to the base and extends upwardly from the base. The spine assembly is mechanically connected to the vertical support rail and is supported by the telescoping tube assembly. The telescoping tube assembly mechanical connects the vertical support rail to the spine assembly. The shelf unit is detachably attachable to the spine assembly and adapted so that when the tray unit is detachably attached to the spine assembly, the shelf unit will remain in a sterile condition even when the rack assembly is not maintained in a sterile condition.

According to a further aspect of the present disclosure, an operating room rack system includes a frame assembly, a telescoping tube assembly, a spine assembly, and an identification assembly. The support frame is mechanically connected to the spine assembly and which pivots about the frame to increase or decrease the angle between the vertical support rail and the spine assembly by extending or collapsing the telescoping tube assembly that is mechanically connected to the frame and spine assembly. The identification assembly is detachably attachable to the spine assembly and adapted so that when the shelf unit is detachably attached to the spine assembly, the shelf unit will remain in a sterile condition even when the rack assembly is not maintained in a sterile condition.

BRIEF DESCRIPTION OF THE SEVERAL VIEWS OF THE DRAWINGS

The present disclosure will be more fully understood and appreciated by reading the detailed description in conjunction with the accompanying drawings and parts list, wherein like reference characters denote similar elements throughout several views:

FIG. 17B is a perspective view of an embodiment of an instrument tray attachment device according to the present disclosure.

FIG. 17C is close up view of an embodiment of an instrument tray attachment device according to the present disclosure in an operational position attached to the rack.

FIG. 17D is an exploded assembly view of an embodiment of an instrument tray attachment device according to the present disclosure

DETAILED DESCRIPTION OF EMBODIMENTS

Figure 1A:
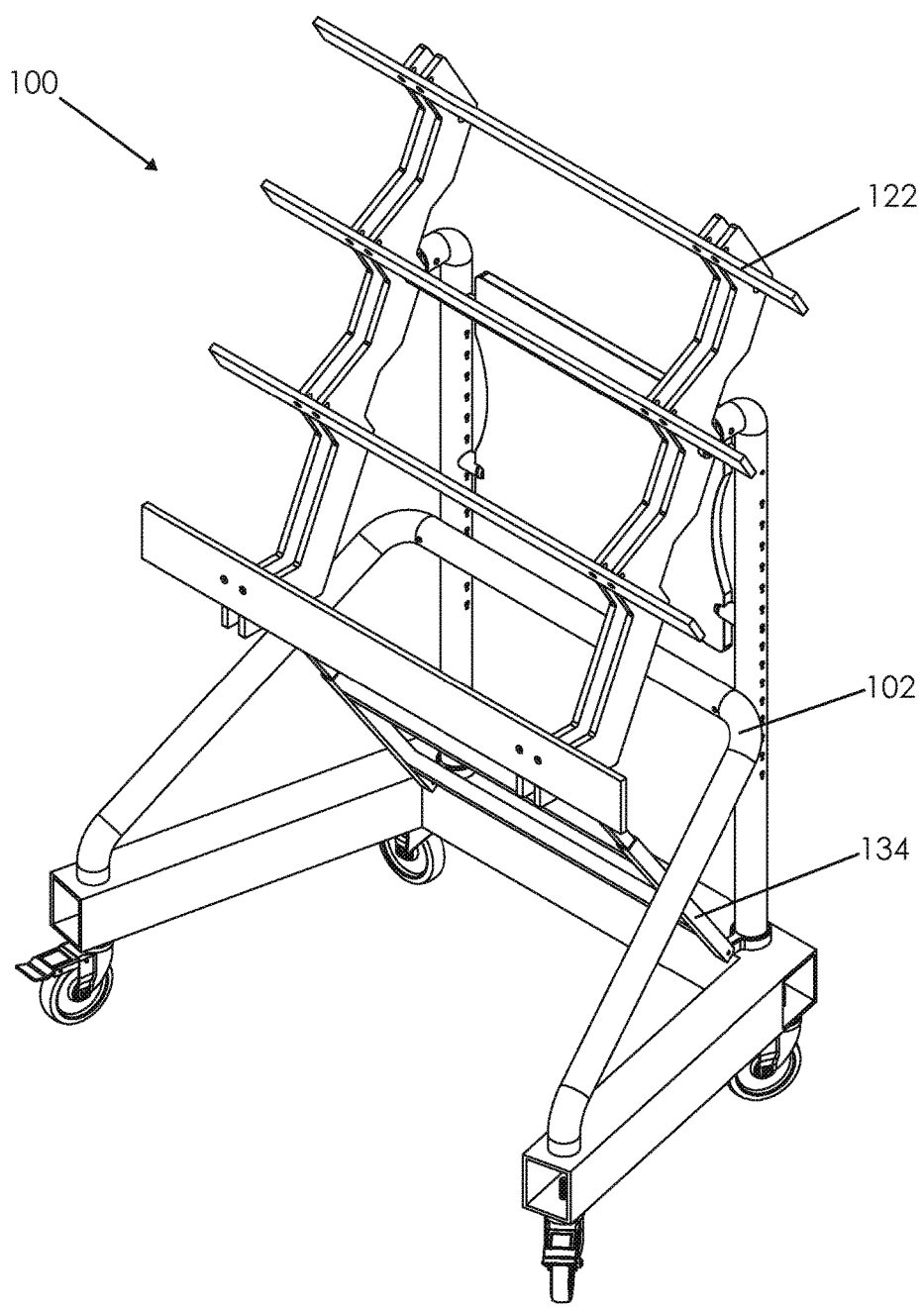
FIG. 1A is a perspective view of a first embodiment of a rack according to the present system with the shelves removed with the rack in an operational position.

Organizational rack system as a cantilever rack 100 is an exemplary embodiment of the present disclosure designed for use in an operating room during surgery to hold surgical instruments. As shown in FIGS. 1 to 16, organizational rack system 100 can include: a frame assembly 102; a spine rail assembly 122; a telescoping tube assembly 134; an interface assembly 144; a tray shelf 150; a receptacle container 152; a primary working shelf 154; a formed base 156; a custom sterile drape 158; an identification assembly 200; a mayo stand attachment 230; a telescoping step stool attachment 240; a light assembly 250; a sterile spray assembly 260; an instrument tray attachment device 270; collapsible cross rail extensions 280; and a ceiling boom assembly 290.

As shown in FIG. 1A, the organizational rack system 100, includes the spine rail assembly 122 that rotates about the frame assembly 102 and is supported by the telescoping tube assembly 134 which is also mechanically connected to the frame assembly. A user can collapse the telescoping tube assembly 134 which decreases the angle between the frame assembly 102 and the spine rail assembly 122 to create a storage position as shown in FIG. 2B.

Figure 2:
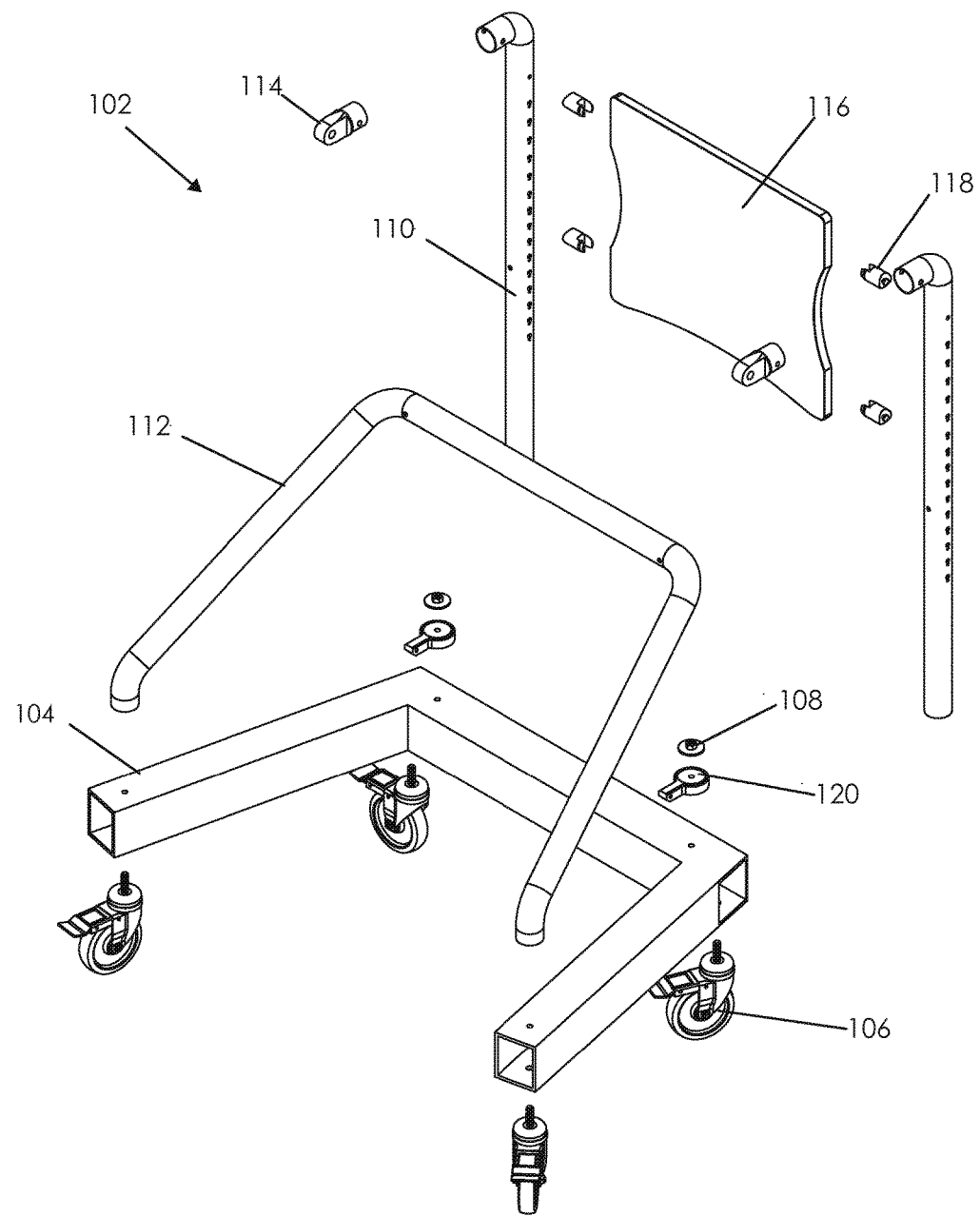
FIG. 2 is an exploded perspective view of a first embodiment of a frame assembly according to the present system.

FIG. 2 shows an exploded assembly of the frame assembly 102. A base 104 is mounted mechanically on two way locking casters 106 to create a platform for a vertical support rail 110 mechanically connected with a tube nut plate insert 108 and is further supported by a radiating support rail 112. A backplane spacer 118 mechanically connects a backplane 116 to the vertical support rail 110. A pivotal or rotational connection, such as a knuckle 114 mechanically connects the spine rail assembly 122 (not pictured) to the vertical support rail 110, and a hinge 120 mechanically connects the telescoping tube assembly 134 (not pictured) to the vertical support rail 110.

Figure 3:
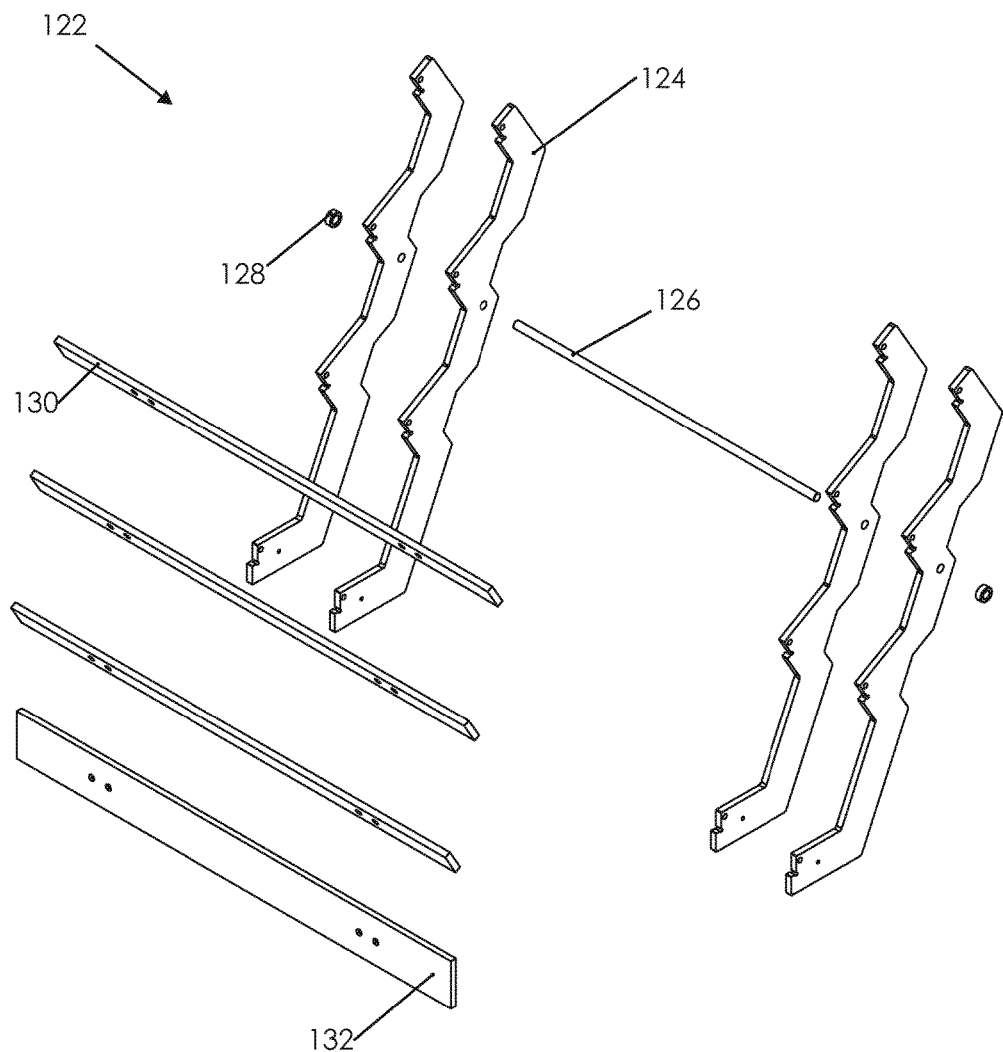
FIG. 3 is an exploded perspective view of a first embodiment of a spine assembly according to the present system.

FIG. 3 shows an exploded assembly of the spine rail assembly for tray shelf support assembly) 122. A shaft 126 mechanically connects the knuckle 114 (not pictured) to the spine 124 and is secured with a coller 128. A bottom cross rail 132 and shelf cross rail 130 are mechanically connected to the vertically-oriented multi-level shelf support panel, or spine 124 at different levels. The spine 124 can be separately adjusted to be orientated at different angles relative to the floor by employing mechanical components able to transfer rotational motion to linear motion such as, but not limited to a system of angled worms and worm gears or a similar system of rack and pinion angle adjustments. (not pictured)

The spine rail assembly 122 includes at least one, and in certain configurations a plurality of shelf cross rails. Each shelf cross rail is configured to operably engage and retain at least one tray shelf 150, thereby associating the tray shelf 150 with a level of the spine 124. While the spines 124 are shown having a plurality of shelf cross rails 130 (and associated tray shelves (not pictured)) at a common mounting angle to the spine, with the bottom cross rail (and associated tray shelf (not pictured)) at a different mounting angle, it is understood, each on different sub combinations, of the shelf cross rails can be a different angles. Typically, the angle of the cross shelf rail 130 the spines 124 is fixed. However, it is understood such angle can be varied or adjustable.

The extending arm assembly can have any of a variety of configurations that provide for the selective elongation (extension) or contraction of the length of the extending arm assembly. Thus, extendable pistons, servers, linear actuators, worm gears or threading can be used to implement the extendable arm assembly. Further, it is contemplative that motors or the servers can be operably connected to the controller, such that the controller can impart movement of the extending arm assembly. For purposes of description, the extending arm assembly is set forth as a telescoping tube assembly. However, it is understood the present system is not limited to a telescoping tube configuration.

Figure 1B:
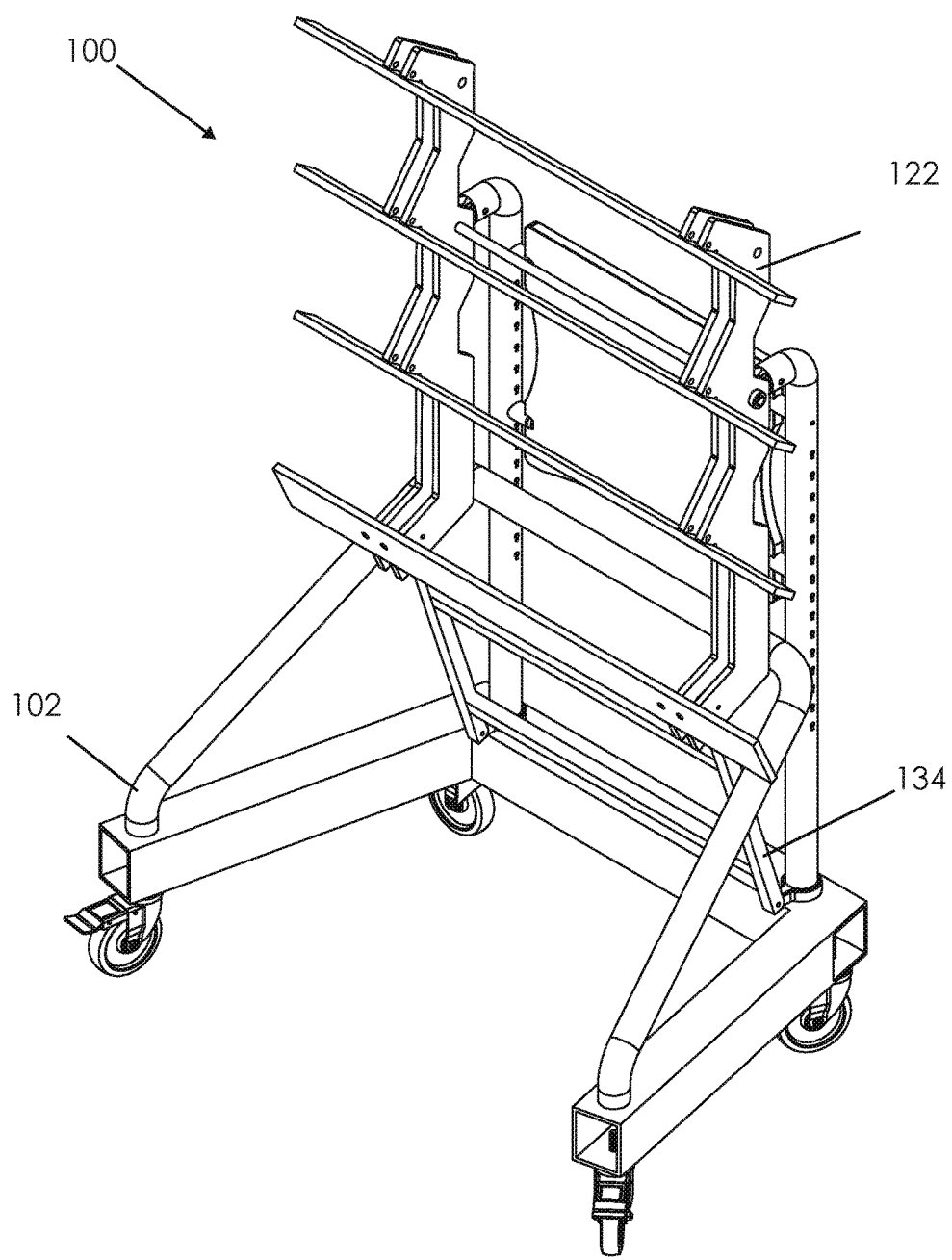
FIG. 1B is a perspective view of a first embodiment of a rack according to the present system with the shelves removed with the rack in a storage position.
Figure 4:
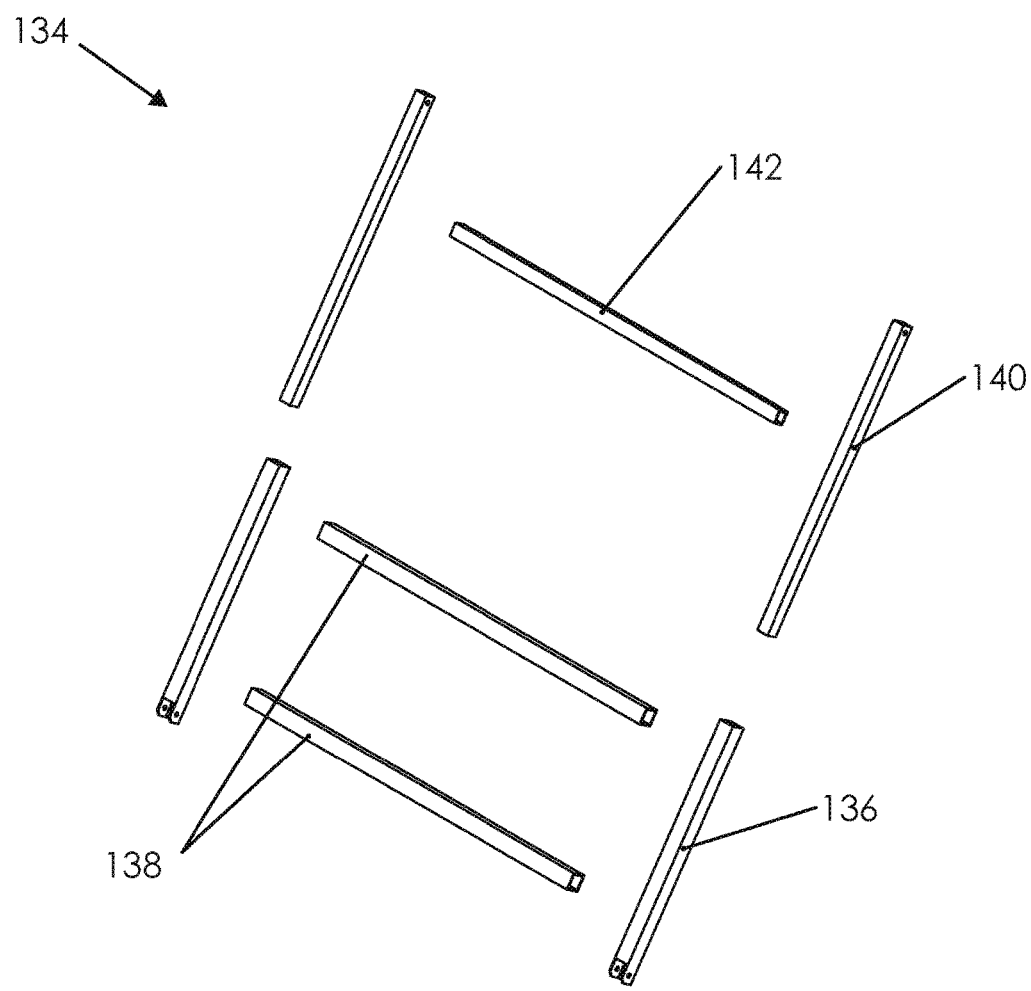
FIG. 4 is an exploded perspective view of a first embodiment of a telescoping tube assembly according to the present system.

FIG. 4 shows an exploded assembly of the telescoping tube assembly 134, which mechanically connects the spine rail assembly 122 to the frame assembly 102 and provides the adjustment to allow for a storage position of the rack 100 as shown in FIG. 1B. A lower slide tube 136 is supported by a lower slide tube cross member 138 so that an upper slide tube 140 which is supported by an upper slide tube cross member 142 can provide the telescoping function.

Figure 5A:
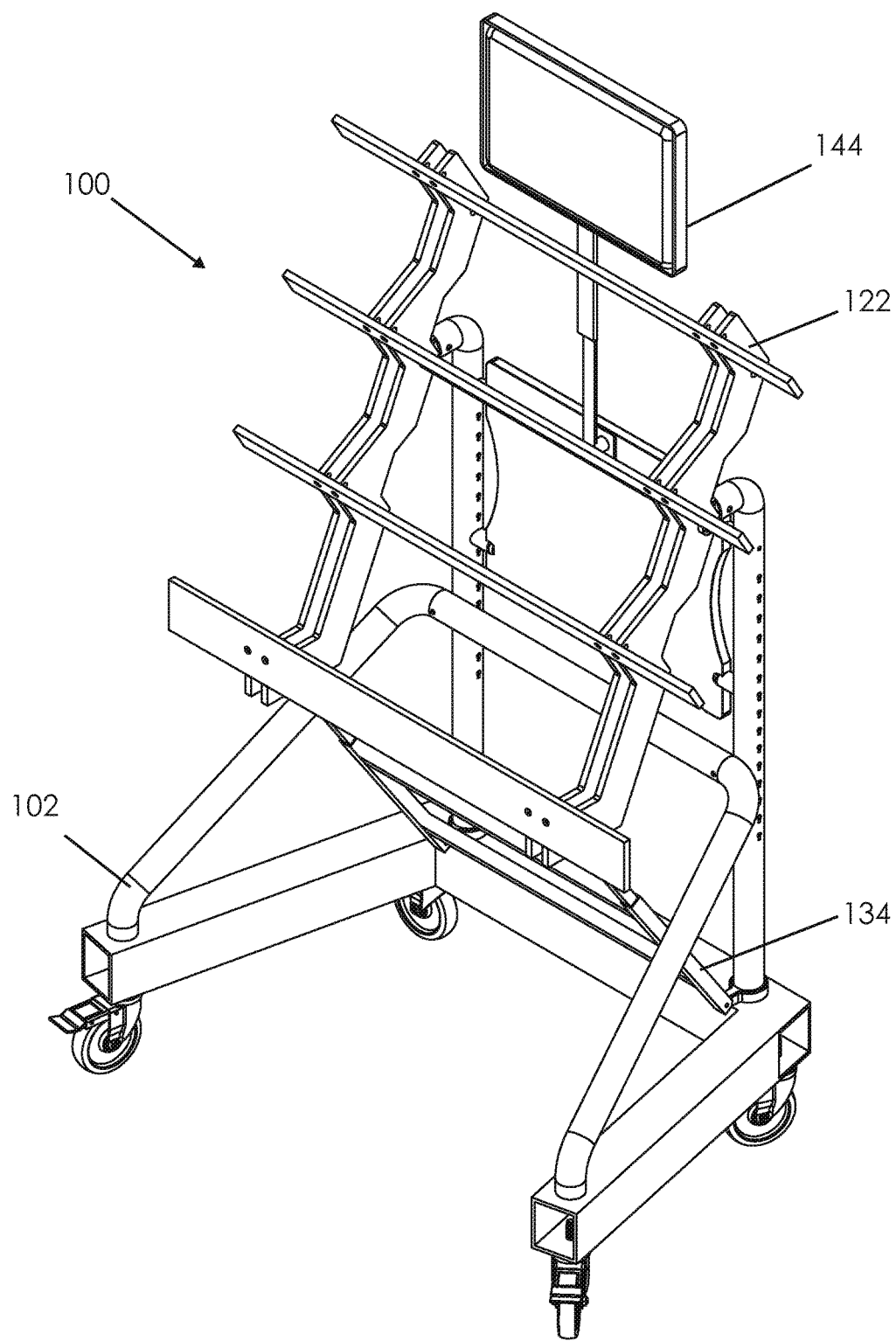
FIG. 5A is a perspective view of a first embodiment of a rack according to the present system with the shelves removed and a user interface in an operational position.
Figure 5B:
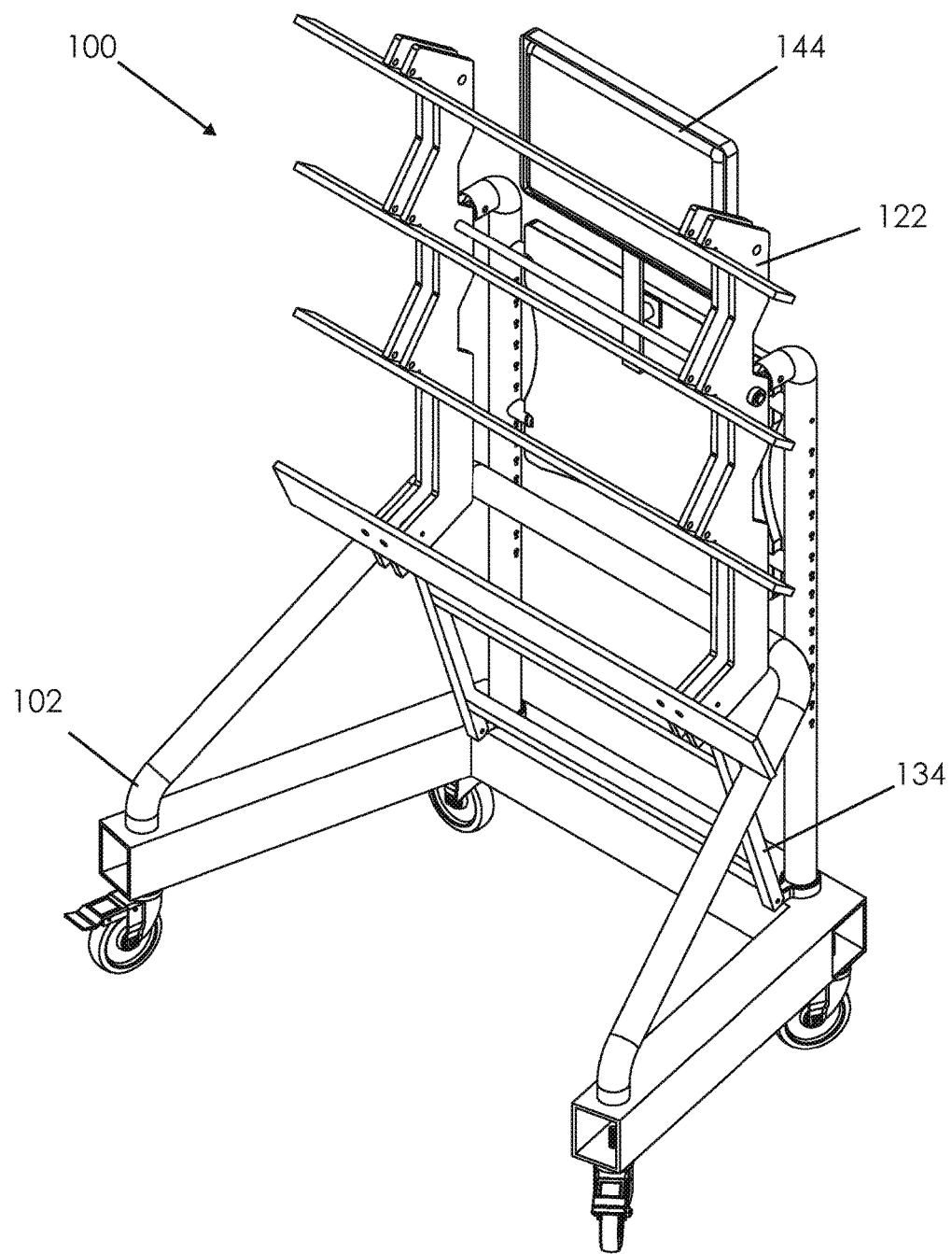
FIG. 5B is a perspective view of a first embodiment of a rack according to the present system with the shelves removed and a user interface a storage position.

As shown in FIG. 5A, the organizational rack system 100, has the spine rail assembly 122 that rotates about the frame assembly 102 and is supported by the telescoping tube assembly 134 which is also mechanically connected to the frame assembly 102. The interface assembly 144 is mechanically connected to the frame assembly 102. A user can collapse the telescoping tube assembly 134 and interface assembly 144 to create a storage position as shown in FIG. 5B.

Figure 6:
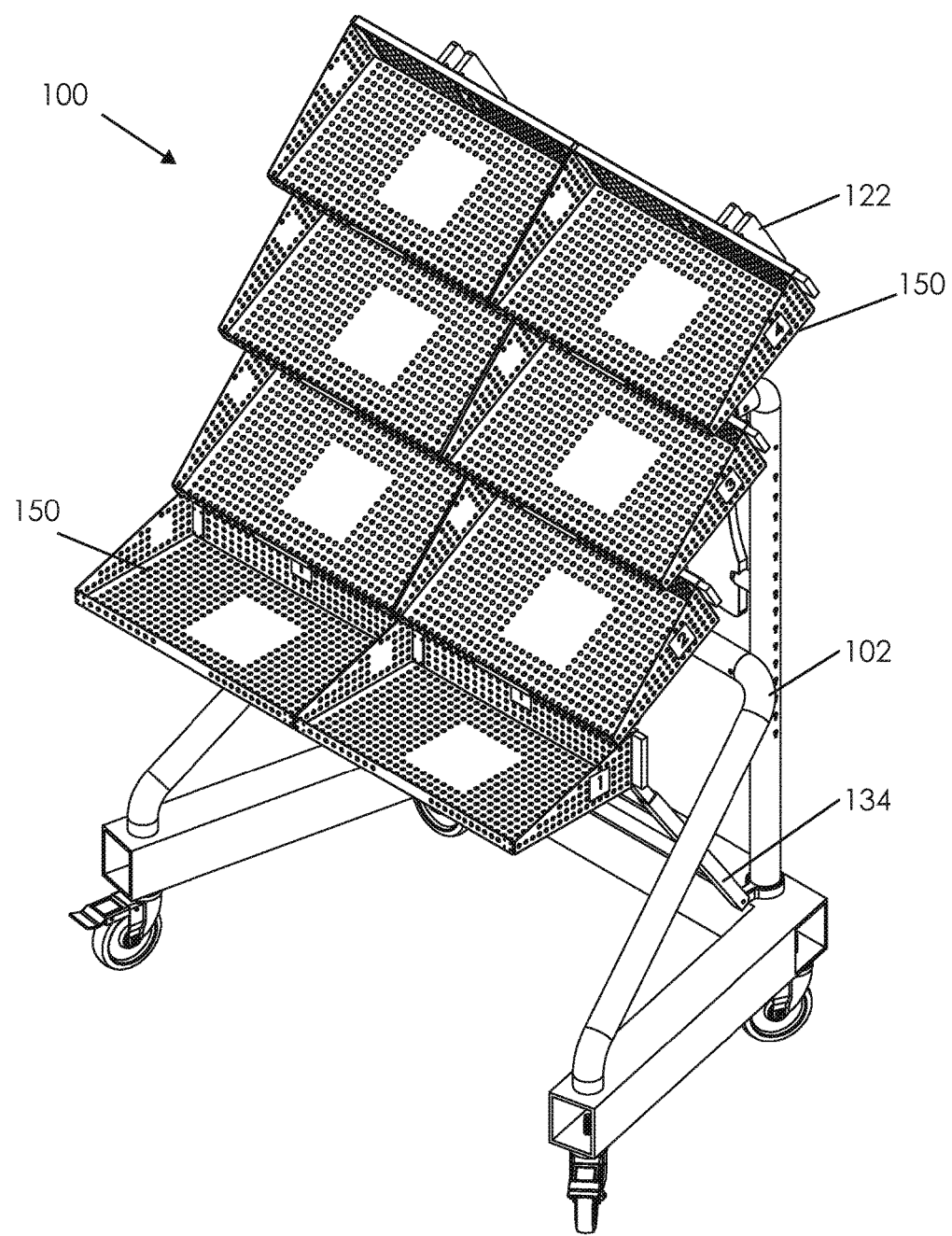
FIG. 6 is a perspective view of a first embodiment of a rack according to the present system with the tray shelves in place and with the rack in an operational position.

As shown in FIG. 6, the organizational rack system 100, has the spine rail assembly 122 that rotates about the frame assembly 102 and is supported by the telescoping tube assembly 134 which is also mechanically connected to the frame assembly 102. The tray shelf 150 is detachable attached by employing specific integrated geometry such as, but not limited to the square J hook attachment on the back edge of tray shelf 150 which is supported by the spine rail assembly 122 and allows for the visible storage of a surgical instrument tray 160 (not pictured) during a procedure.

Figure 7:
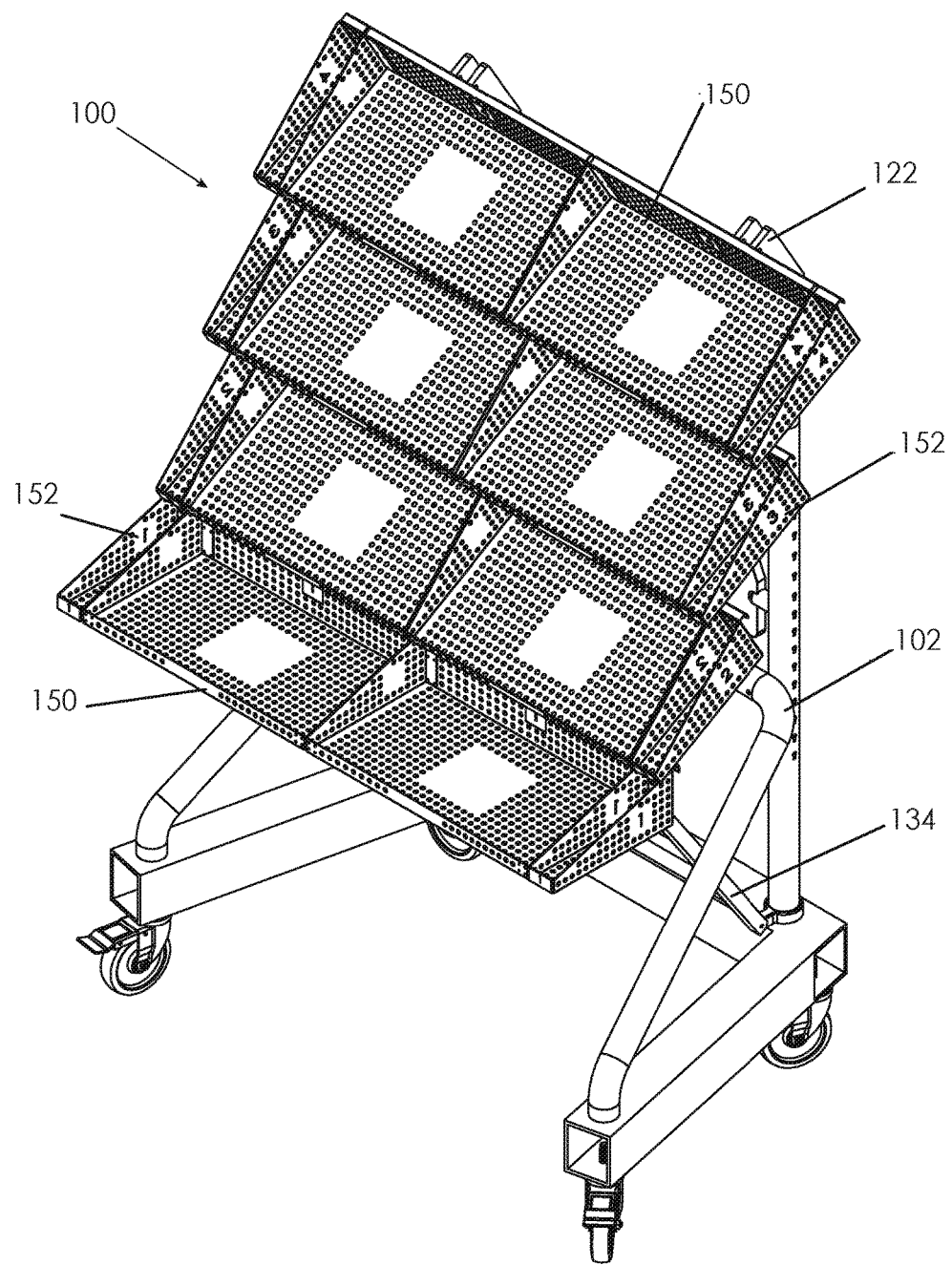
FIG. 7 is a perspective view of a first embodiment of a rack according to the present system with the tray shelves and receptacle shelves in place.

As shown in FIG. 7, the organizational rack system 100, has the spine rail assembly 122 that rotates about the frame assembly 102 and is supported by the telescoping tube assembly 134 which is also mechanically connected to the frame assembly 102. The tray shelf 150 and a receptacle container 152 are detachable attached to the spine rail assembly 122 by employing specific integrated geometry such as, but not limited to the square J hook attachment on the back edge of tray shelf 150 and receptacle container 150. The containment receptacle 152 allows for the storage of used surgical instruments with liquid during a procedure so as not to infringe on protocol while maintaining instrument correlation with its specified location. The tray shelf 150 and receptacle container 152 can be integral or separate compartments.

Figure 8A:
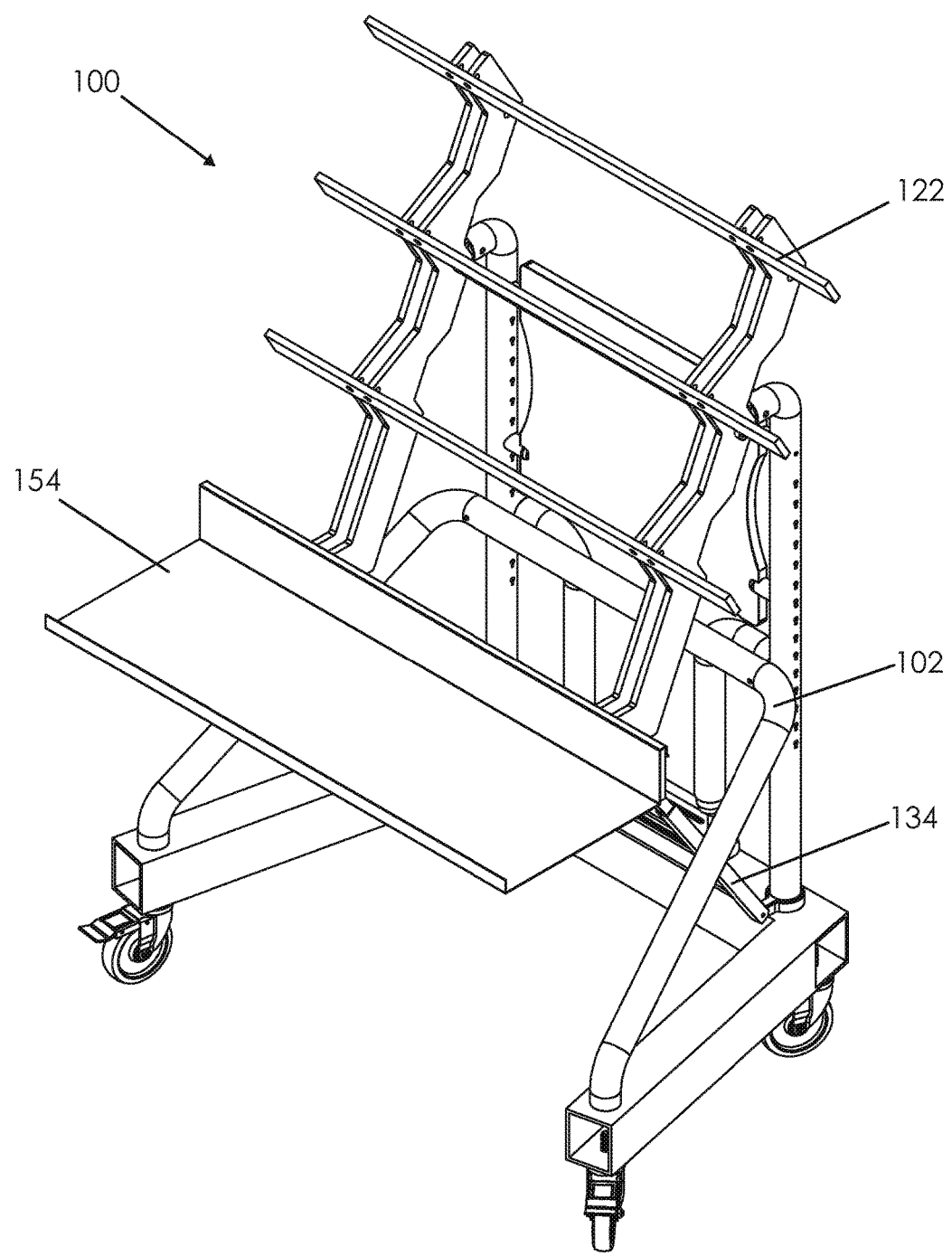
FIG. 8A is a perspective view of a first embodiment of a rack according to the present system with the primary working shelf in an operational position.
Figure 8B:
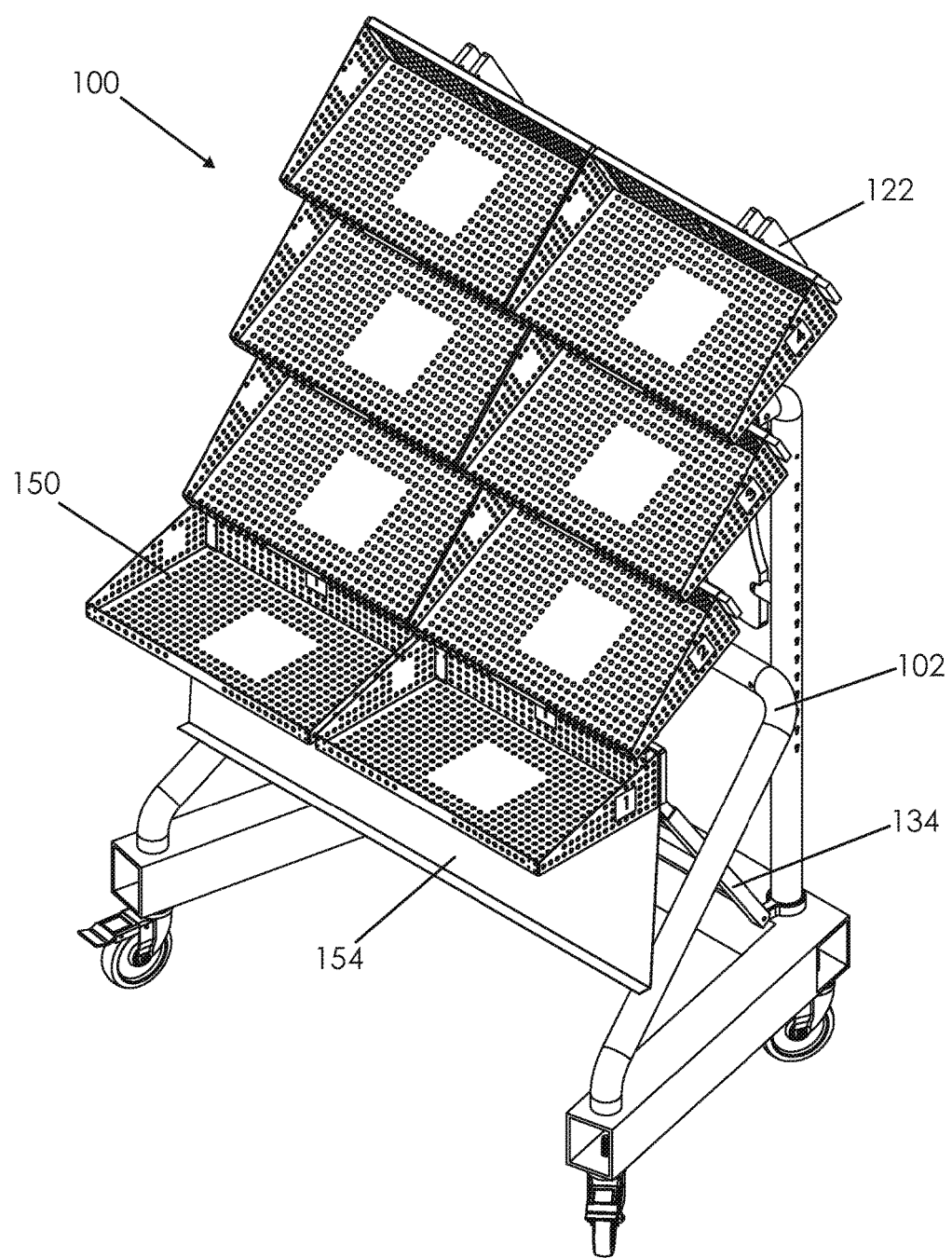
FIG. 8B is a perspective view of a first embodiment of a rack according to the present system with the tray shelves in an operational position and the primary working shelf in a storage position.

As shown in FIG. 8A, the organizational rack system 100, has the spine rail assembly 122 that rotates about the frame assembly 102 and is supported by the telescoping tube assembly 134 which is also mechanically connected to the frame assembly 102. A primary working shelf 154 is mechanically connected to the spine rail assembly 122 so that it provides an enlarged work space to be used as needed. A user can collapse the primary working shelf 154 by employing a collapsible linkage support such as, but not limited to a drop leaf mechanism with or without hydraulic qualities (not pictured). The tray shelf 150 may be attached to spine rail assembly 122 without having to remove the primary working shelf 154 by employing specific integrated geometry such as, but not limited to the square J hook attachment on the back edge of tray shelf 150, seen in FIG. 8B.

Figure 9:
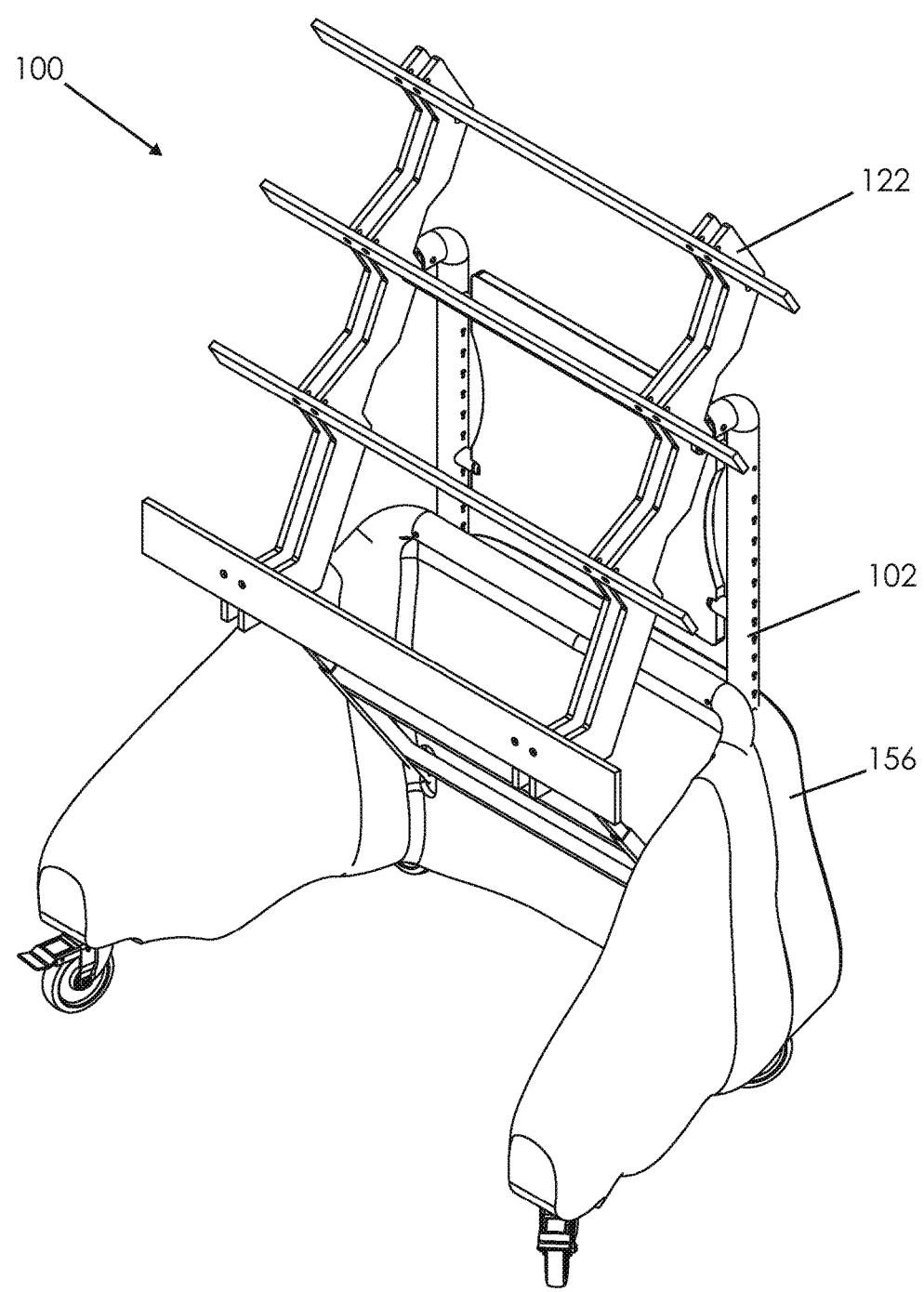
FIG. 9 is a perspective view of a first embodiment of a rack according to the present system with the shelves removed and a formed base in place.

FIG. 9 shows the organizational rack system 100 and the spine rail assembly 122 that rotates about the frame assembly 102 and is supported by the telescoping tube assembly 134 and a formed base cowling 156 to add a stylized piece that can be customized for the system 100.

Figure 10:
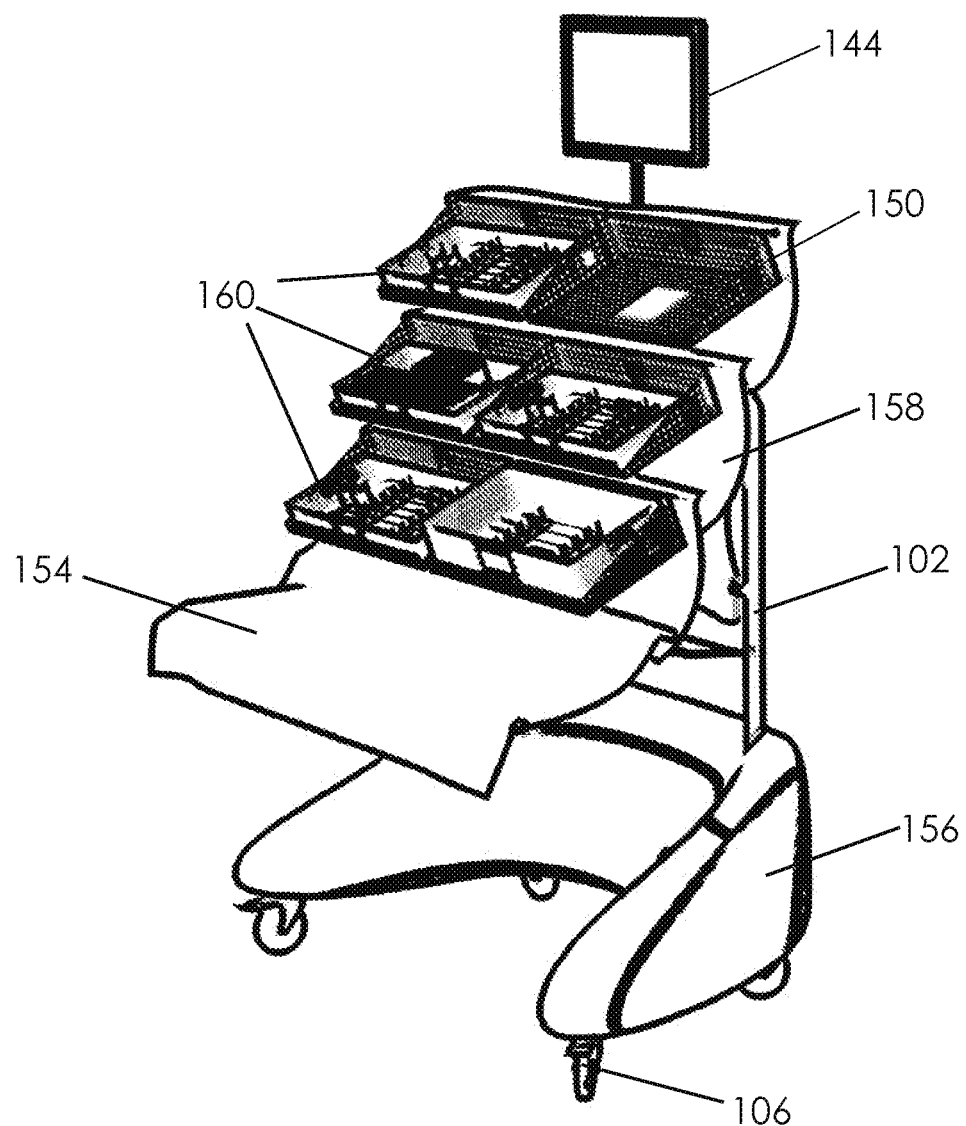
FIG. 10 is a perspective view of a first embodiment of a rack according to the present system in an operational position with the user interface, instrument trays inside the tray shelves, and primary shelf working shelf in an operation position and the custom sterile drape in place.
Figure 11:
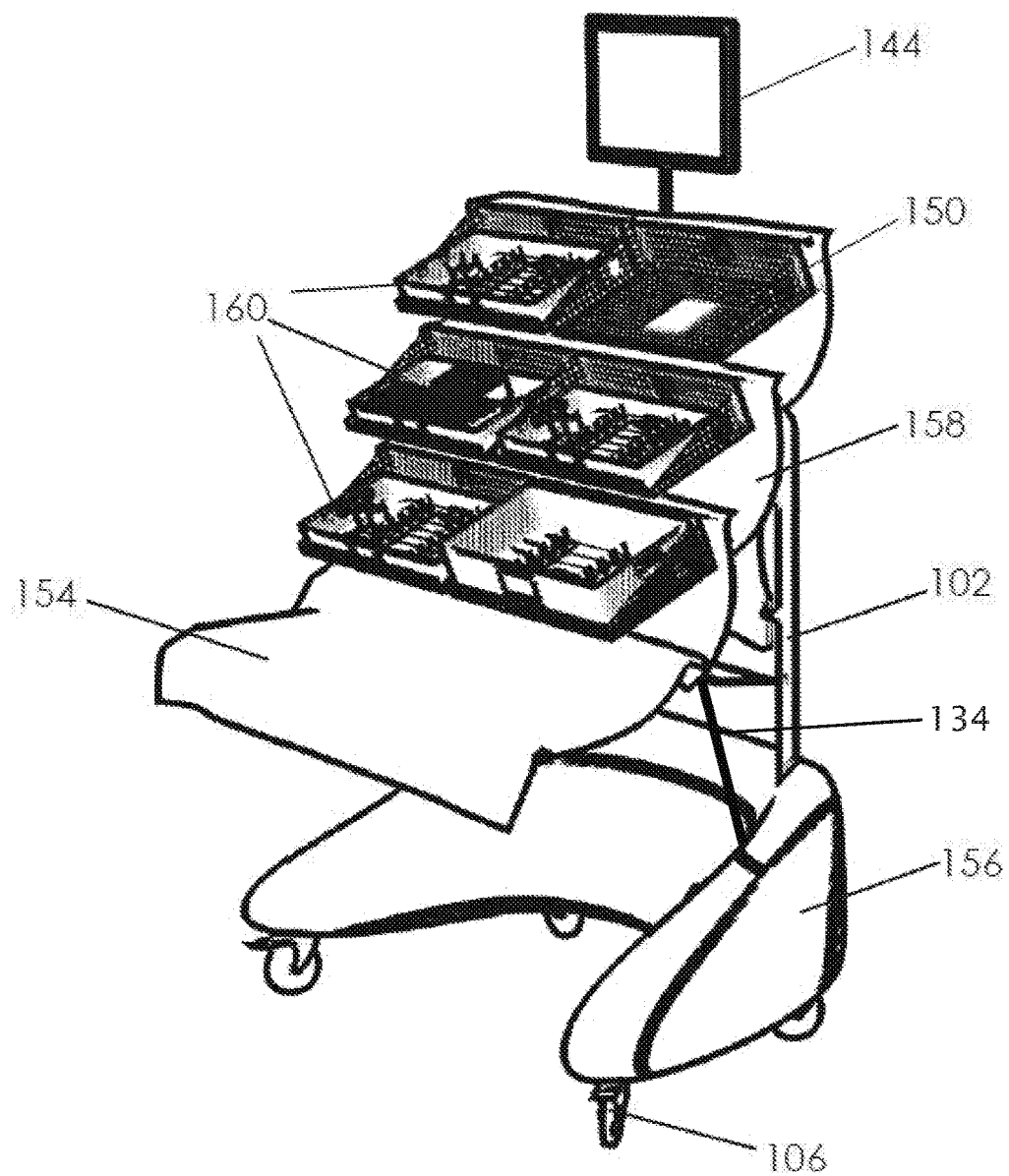
FIG. 11 is a perspective view of the embodiment of the rack of FIG. 10 showing a telescoping tube assembly.

One embodiment of the cantilever organizational rack system 100 is shown in FIG. 10 with the caster 106 protruding from the stylized base cowling 156, the frame assembly 102 supporting the interface assembly 144 and a custom drape 158 that maintains the sterility of the rack 100 and the primary working shelf 154. That is, the drape 158 forms a barrier between the tray shelves 150 (with the accompanying instrument trays 160) and the remainder of the organizational rack system 100.

Figure 12A:
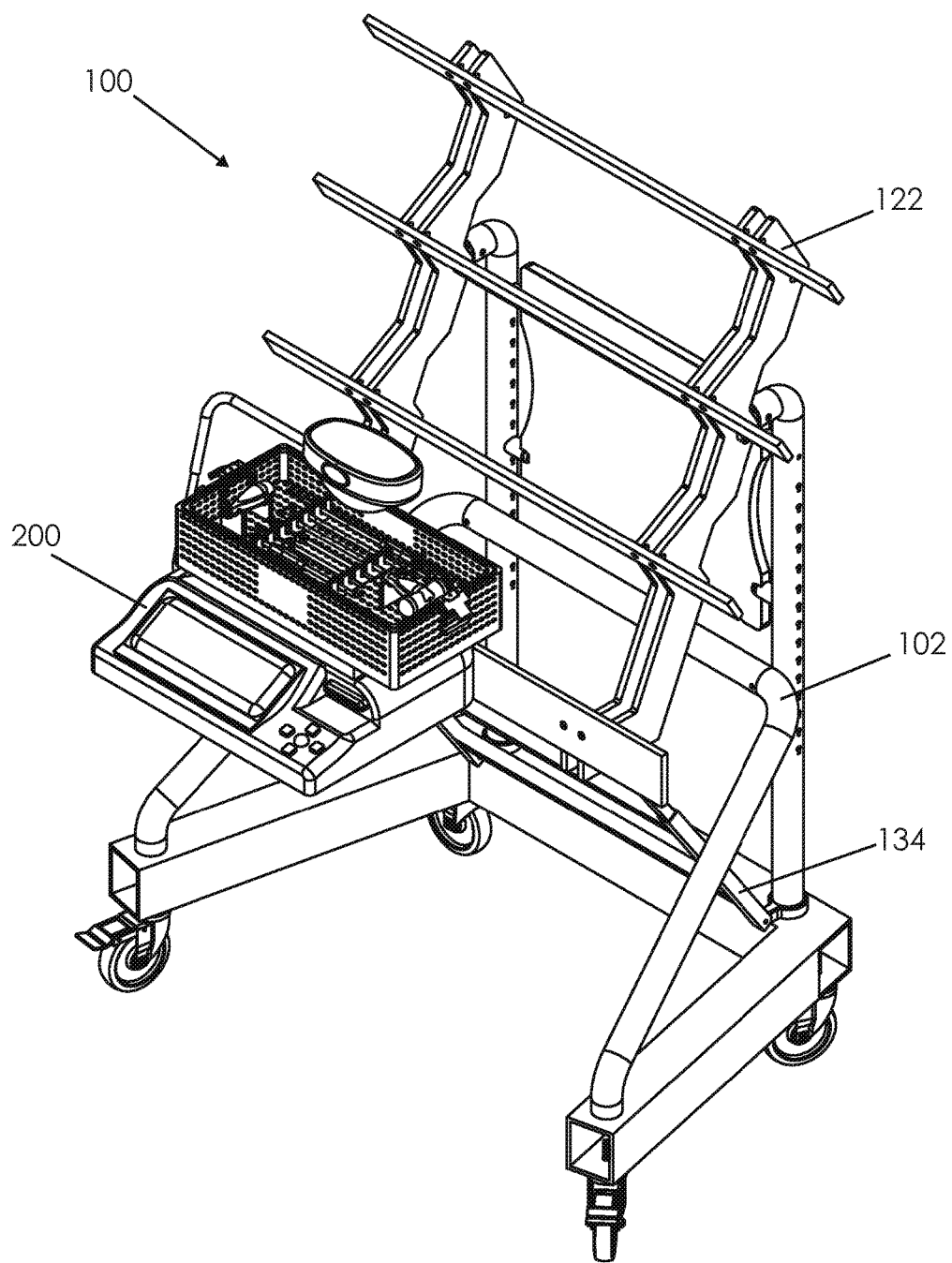
FIG. 12A is a perspective view of an embodiment of a rack according to the present system with an identification assembly attached to the rack.

FIG. 12A shows a organizational rack system 100 and the spine rail assembly 122 that rotates about the frame assembly 102 and is supported by the telescoping tube assembly 134 which is also mechanically connected to the frame assembly 102 and an identification assembly 200.

Figure 12B:
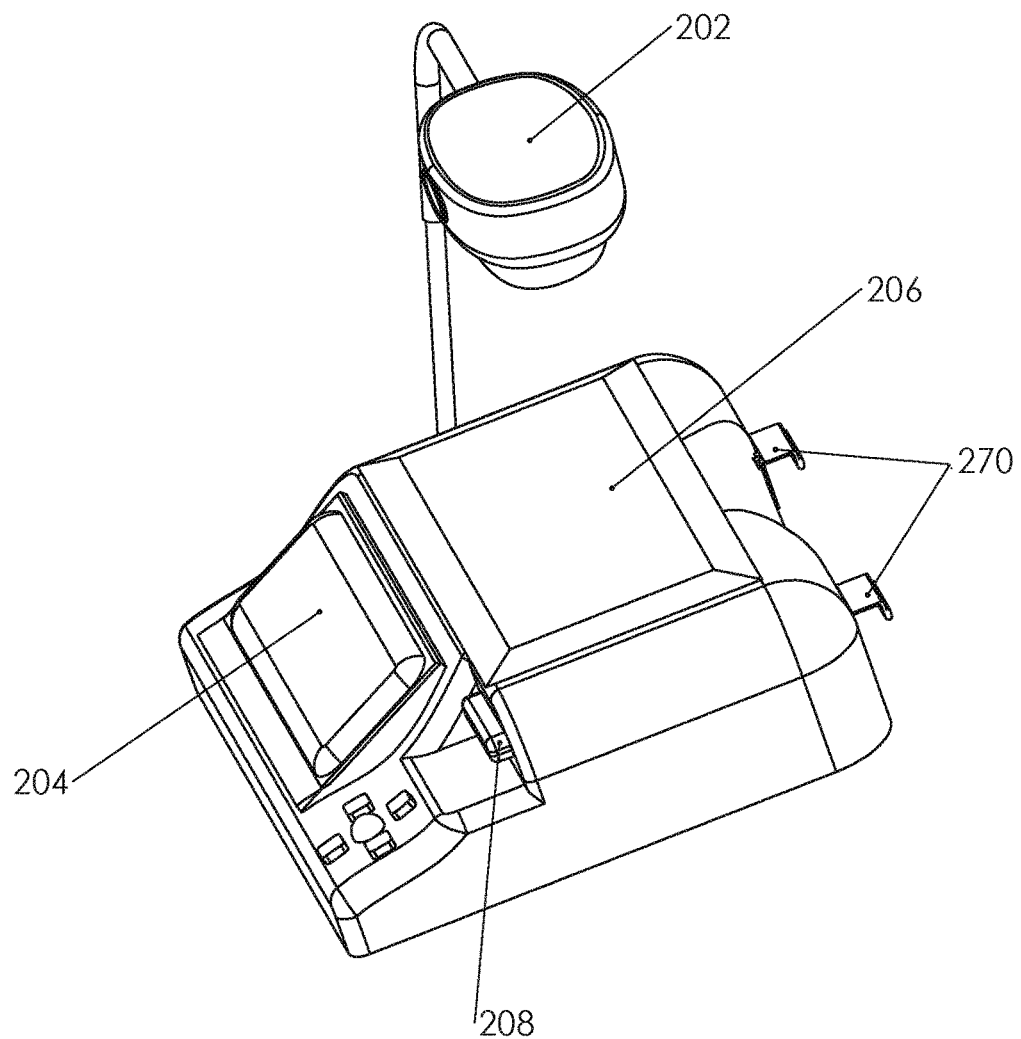
FIG. 12B. is a perspective view of an embodiment of an identification system according to the present disclosure.

As shown in FIG. 12B, the identification assembly 200 is comprised not inclusively nor limited to a camera, a scanner 202, an identification interface 204, a scale 206, a label printer 208 and attachment latch 270 which provides the support necessary to mount the identification assembly 200 onto spine rail assembly 122 (not pictured).

Figure 13A:
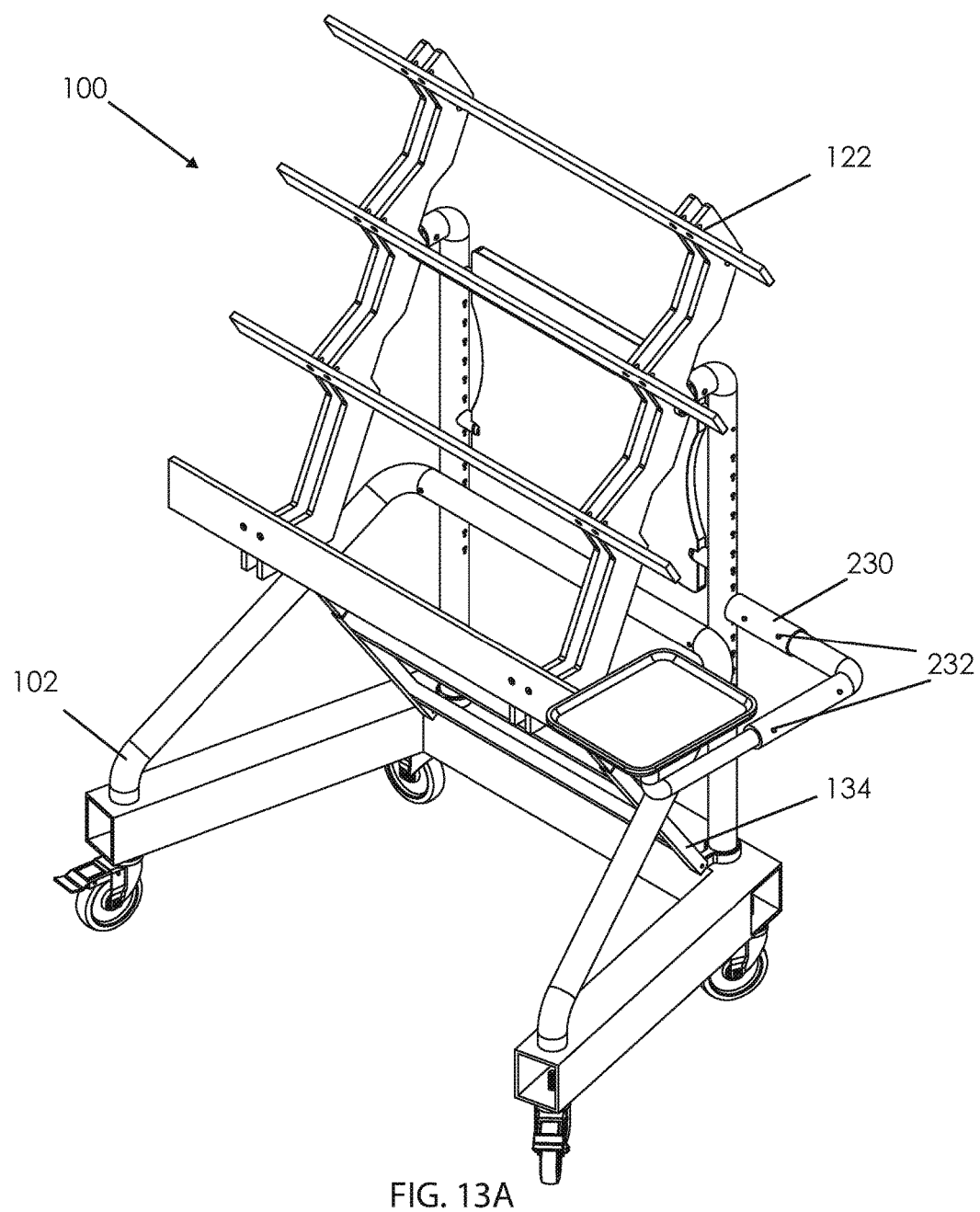
FIG. 13A is perspective view of an embodiment of a mayo stand attachment device in an operation position.
Figure 13B:
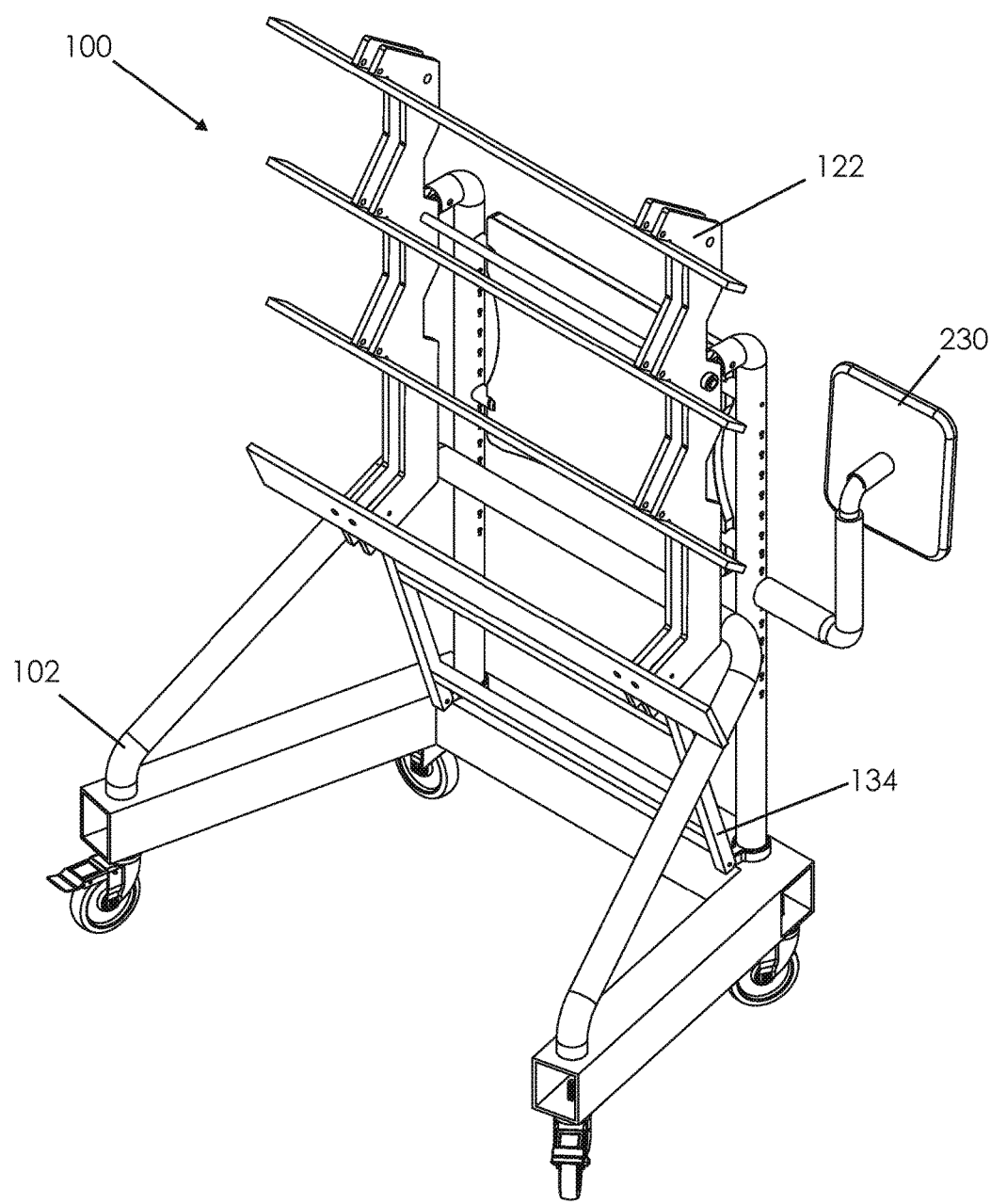
FIG. 13B is perspective view of an embodiment of mayo stand attachment device in a storage position.

As shown in FIG. 13A, a cantilever rack 100, has the spine rail assembly 122 that rotates about the frame assembly 102 and is supported by the telescoping tube assembly 134 which is also mechanically connected to the frame assembly 102 and a mayo stand attachment 230 which can be detachable attached to the frame assembly 102 by employing mechanical features such as, but not limited to a tear drop interface between frame assembly 102 and mayo stand attachment 230. A user can collapse the mayo stand attachment 230 by depressing the spring loaded pin 232 and subsequently maneuvering with linear and rotating movements relative to the frame assembly 102 in order to accommodate a storage position as shown in FIG. 13B.

Figure 14A:
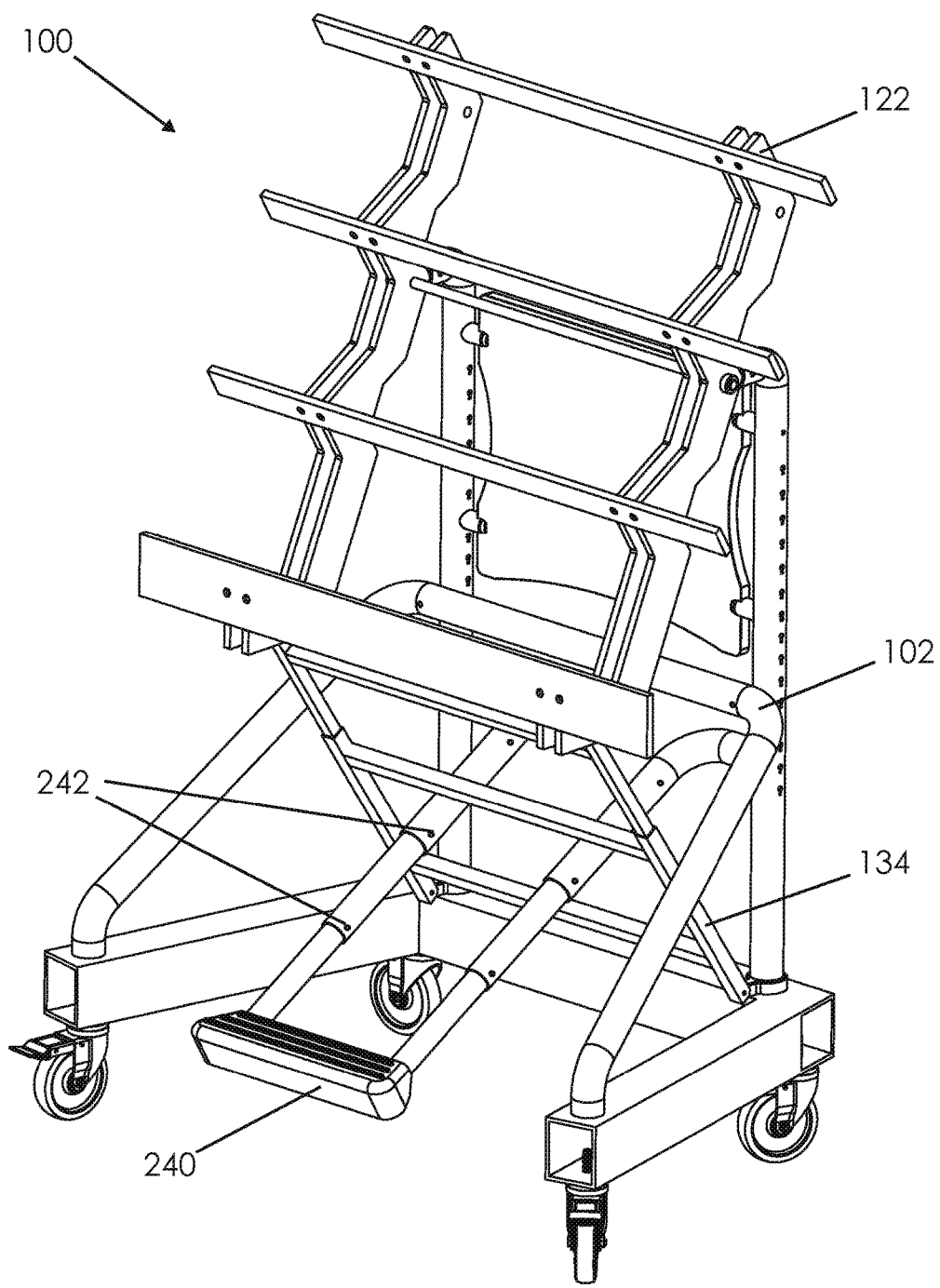
FIG. 14A is perspective view of an embodiment of a telescoping step stool attachment device in an operation position.
Figure 14B:
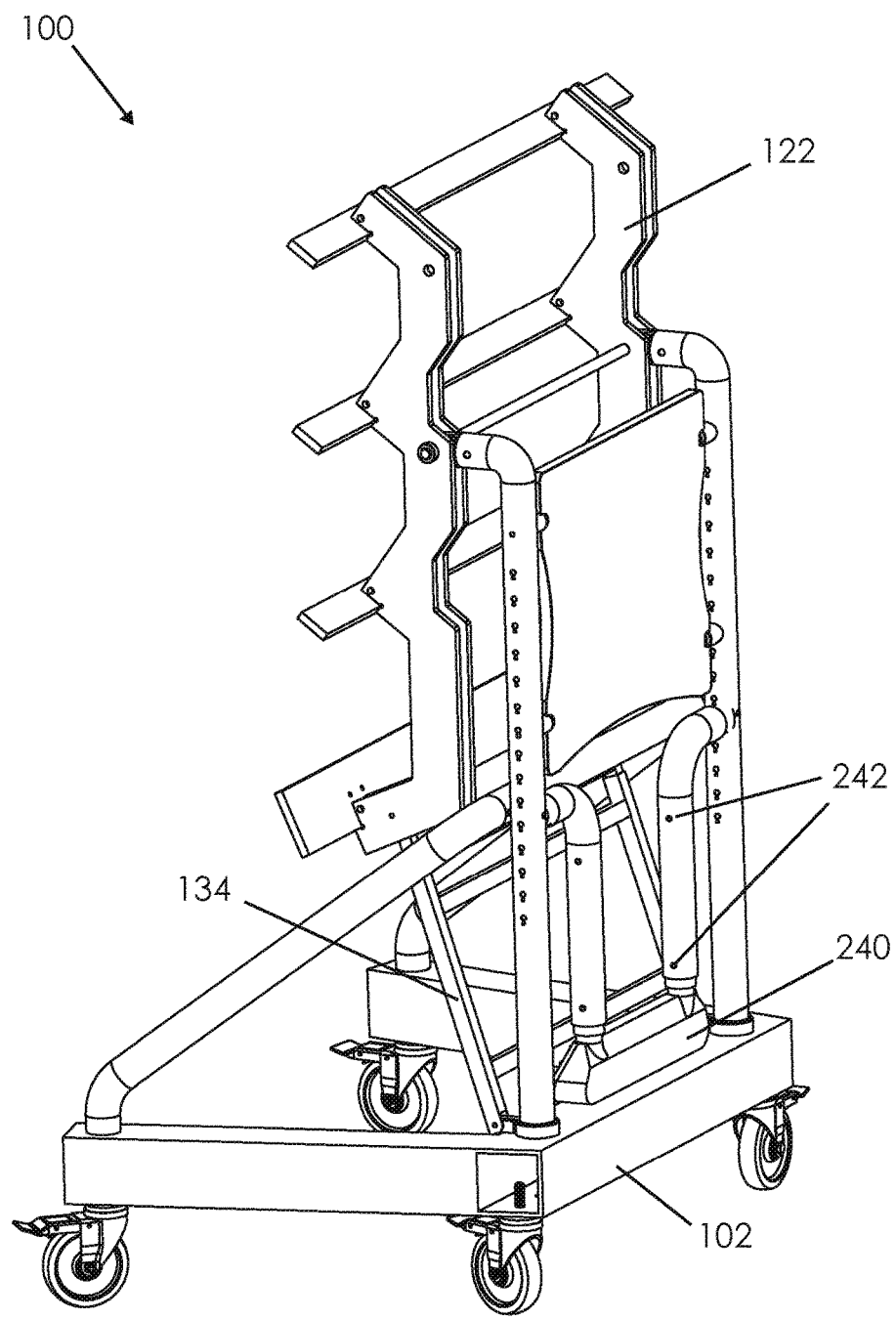
FIG. 14B is perspective view of an embodiment of a telescoping step stool attachment device in a storage position.

As shown in FIG. 14A, the organizational rack system 100, has the spine rail assembly 122 that rotates about the frame assembly 102 and is supported by the telescoping tube assembly 134 which is also mechanically connected to the frame assembly 102 and the telescoping step stool attachment 240 which can be detachable attached to the frame assembly 102 by employing mechanical features such as, but not limited to a tear drop interface between frame assembly 102 and step stool attachment 240. The step stool attachment can accommodate a user of five feet or less by providing a vertical boost in order to gain access to the upper most tray shelf 150 with reduced physical strain. The telescoping step stool 240 can also collapse to allow for a storage position as shown in FIG. 14B. While set forth as a telescoping step stool 240, it is understood any extending linkage construction can be employed, such as, but not limited to a series of sequentially smaller structural members so that each member moves freely inside the sequentially larger member and outside the sequentially smaller member in series. Each structural member is held in the desired position of use or storage by employing the spring loaded pin 242.

Figure 15A:
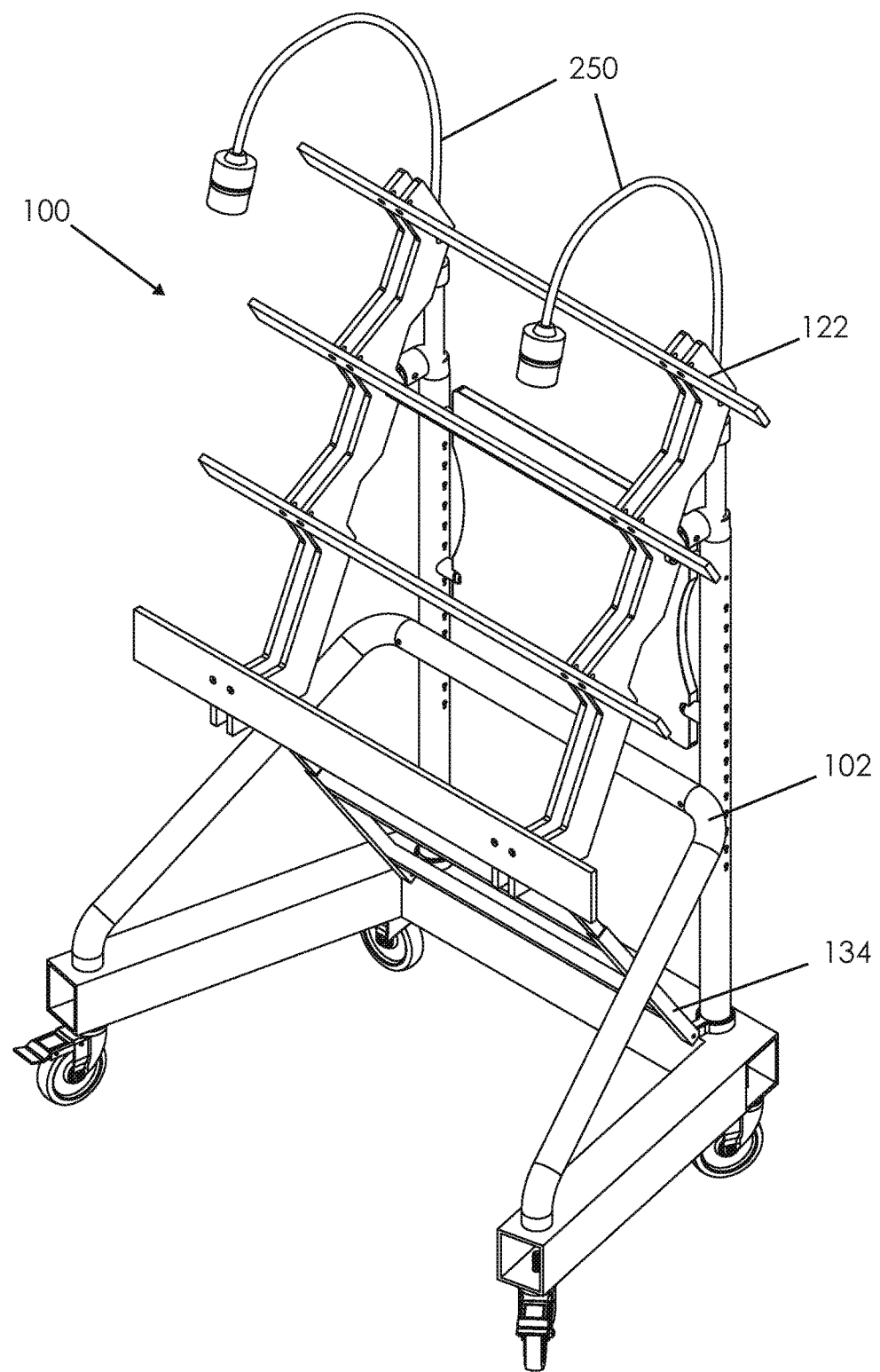
FIG. 15A is perspective view of an embodiment of a light assembly attachment device in an operation position.
Figure 15B:
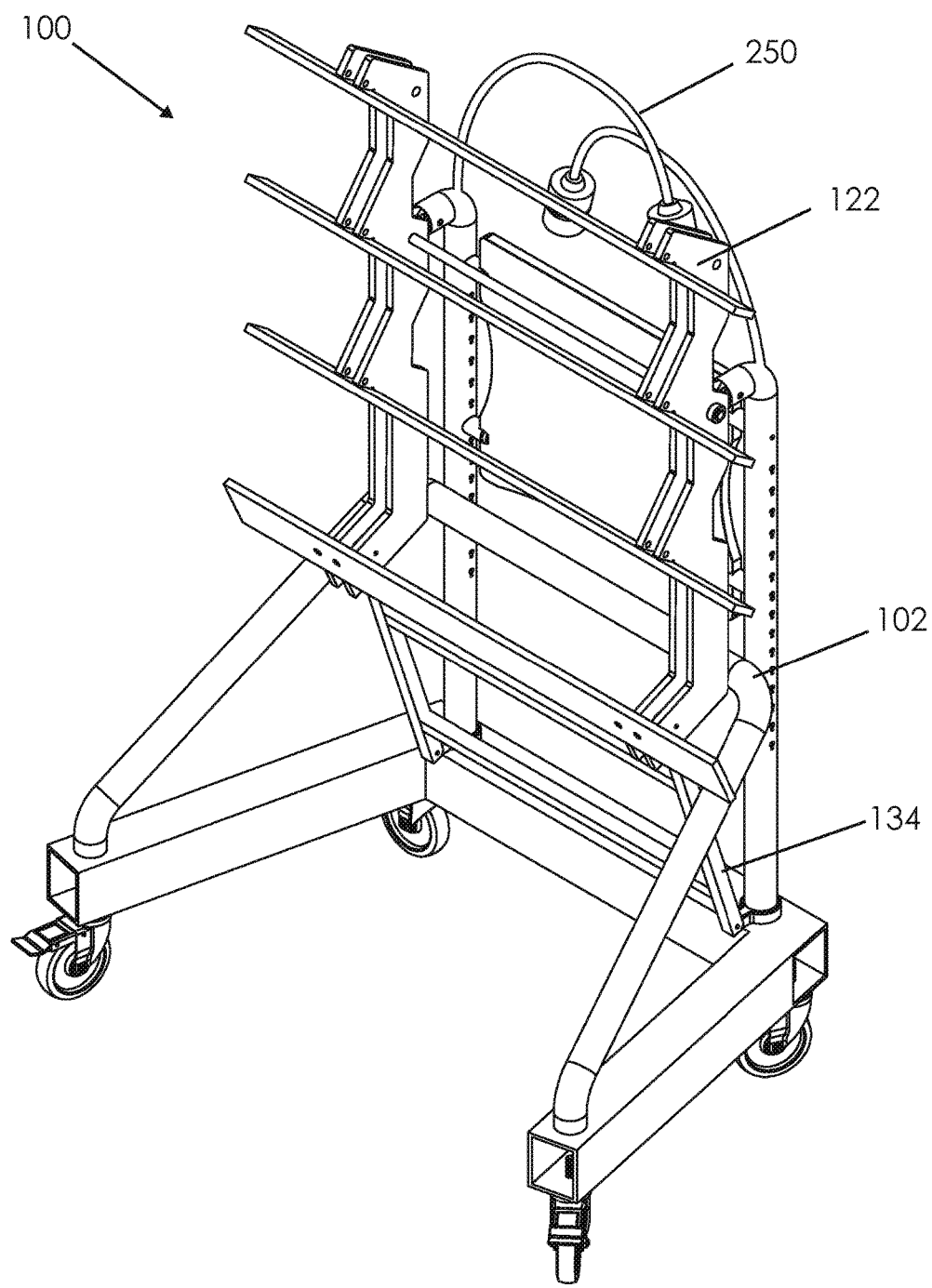
FIG. 15B is perspective view of an embodiment of a light assembly attachment device in a storage position.

As shown in FIG. 15A, a cantilever rack 100 has the spine rail assembly 122 that rotates about the frame assembly 102 and is supported by the telescoping tube assembly 134 which is also mechanically connected to the frame assembly 102 and light assembly 250 which can be detachable attached to the frame assembly 102 and can provide extra light when necessary. The light assembly 250 gets the necessary power transmittance from sufficient gaged electrical wire running interiorly to the frame assembly 102 with the male plug (not pictured) located in a reasonably accessible location as to not interfere with caster 106. A user can collapse the light assembly 250 by adjusting the gooseneck or similar flexible mounting arm of the light assembly 250 in order to accommodate a storage position as shown in FIG. 15B.

Figure 16A:
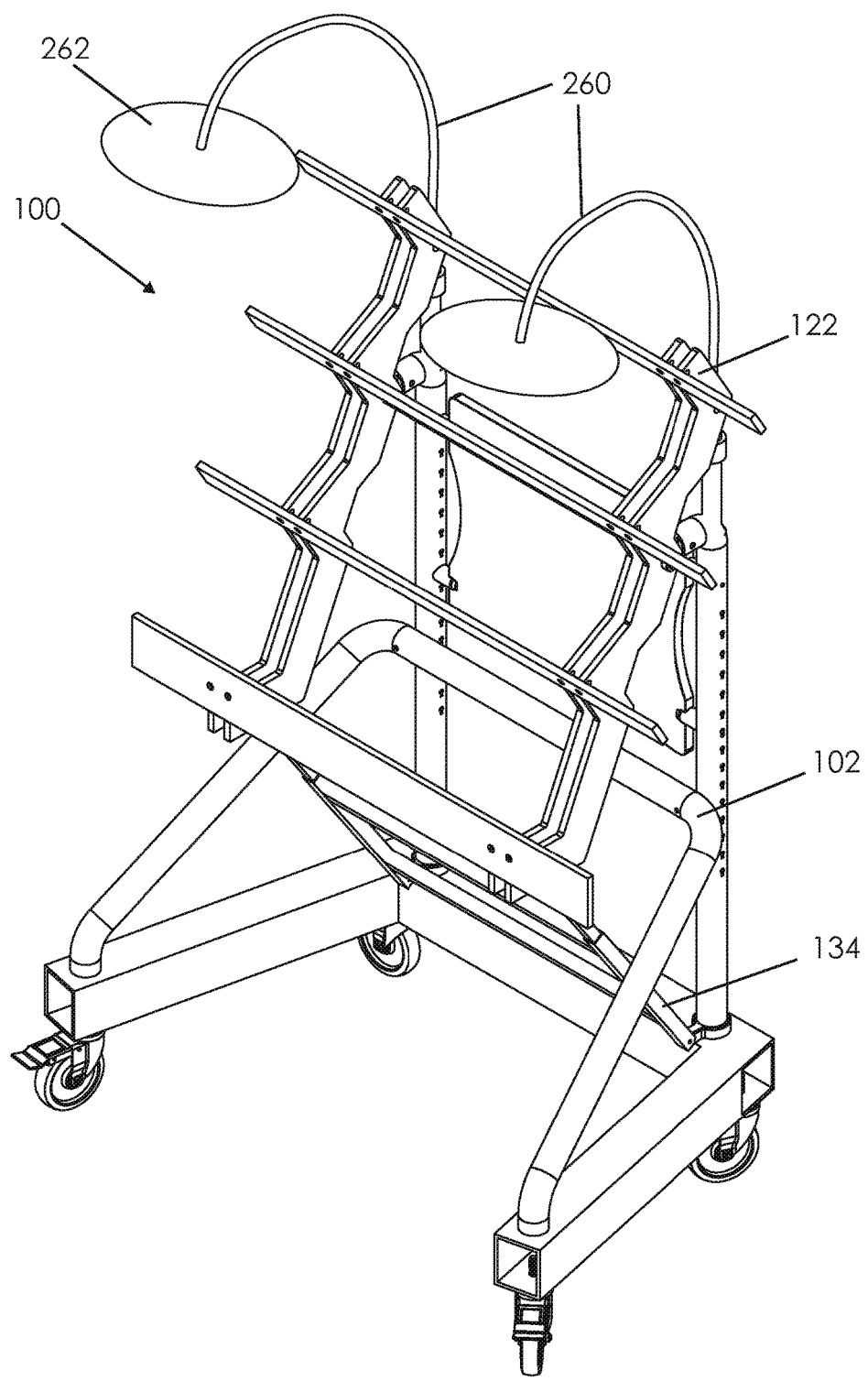
FIG. 16A is perspective view of an embodiment of a sterile sprayer assembly attachment device in an operation position.
Figure 16B:
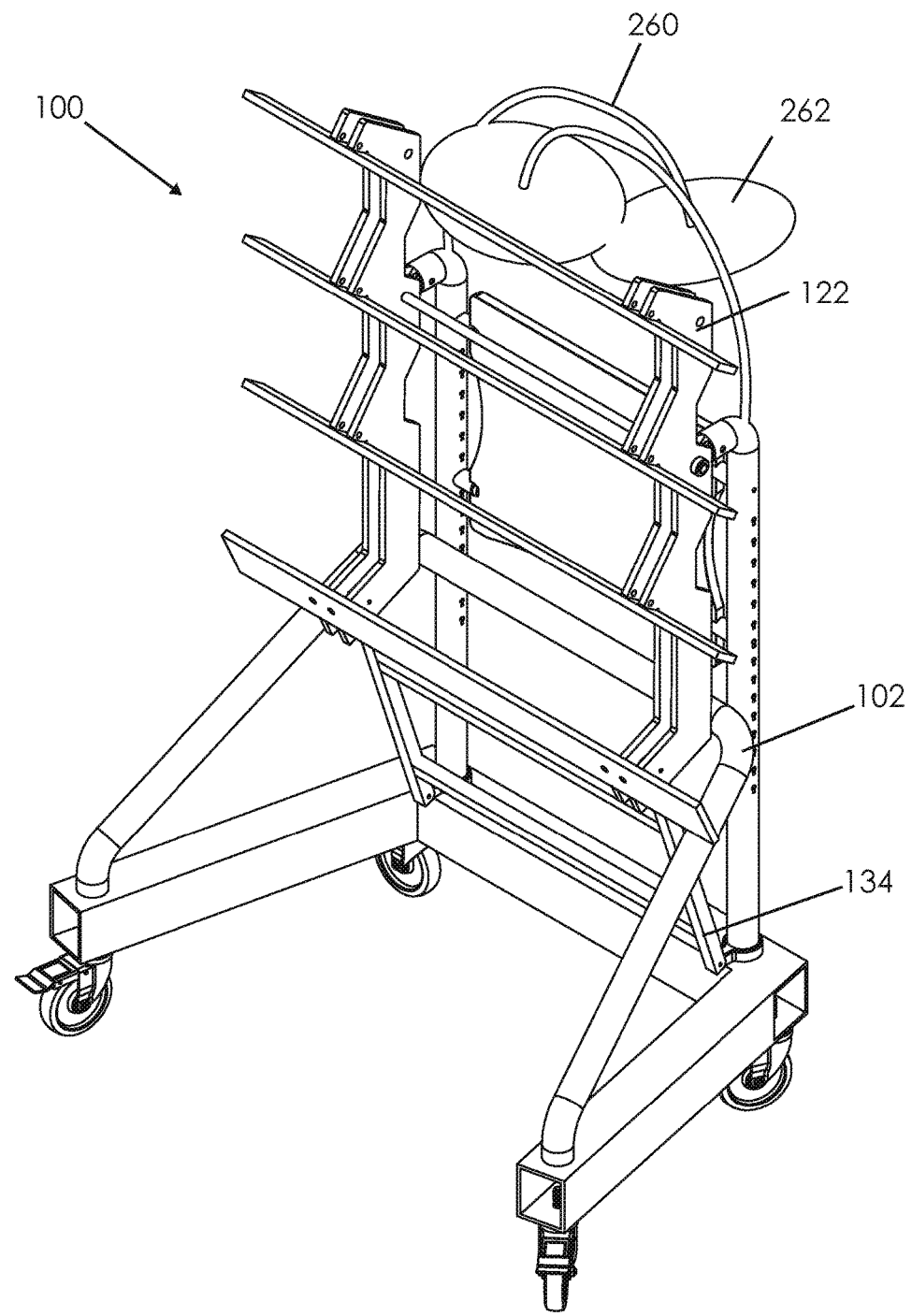
FIG. 16B is perspective view of an embodiment of a sterile sprayer assembly attachment device in a storage position.

As shown in FIG. 16A, the organizational rack system 100, has the spine rail assembly 122 that rotates about the frame assembly 102 and is supported by the telescoping tube assembly 134 which is also mechanically connected to the frame assembly 102 and the sterile spray assembly 260 which can be detachable attached to the frame assembly 102 and provide an aerosol that increases sterility of surgical instruments. The sterilant is stored in a pressurized container (not pictured) housed inside the frame assembly 102 and upon a manual activation such as, but not limited to a valve or push button (not pictured) the pressurized sterilant is forced to the atomizer 262 creating a blanket of sterile aerosol that falls on to the instrument tray 160 (not pictured). The sterile spray assembly 260 can be collapsed by adjusting the gooseneck or similar flexible mounting arm of the sterile spray assembly 260 in order to accommodate to accommodate a storage position as shown in FIG. 16B.

Figure 17A:
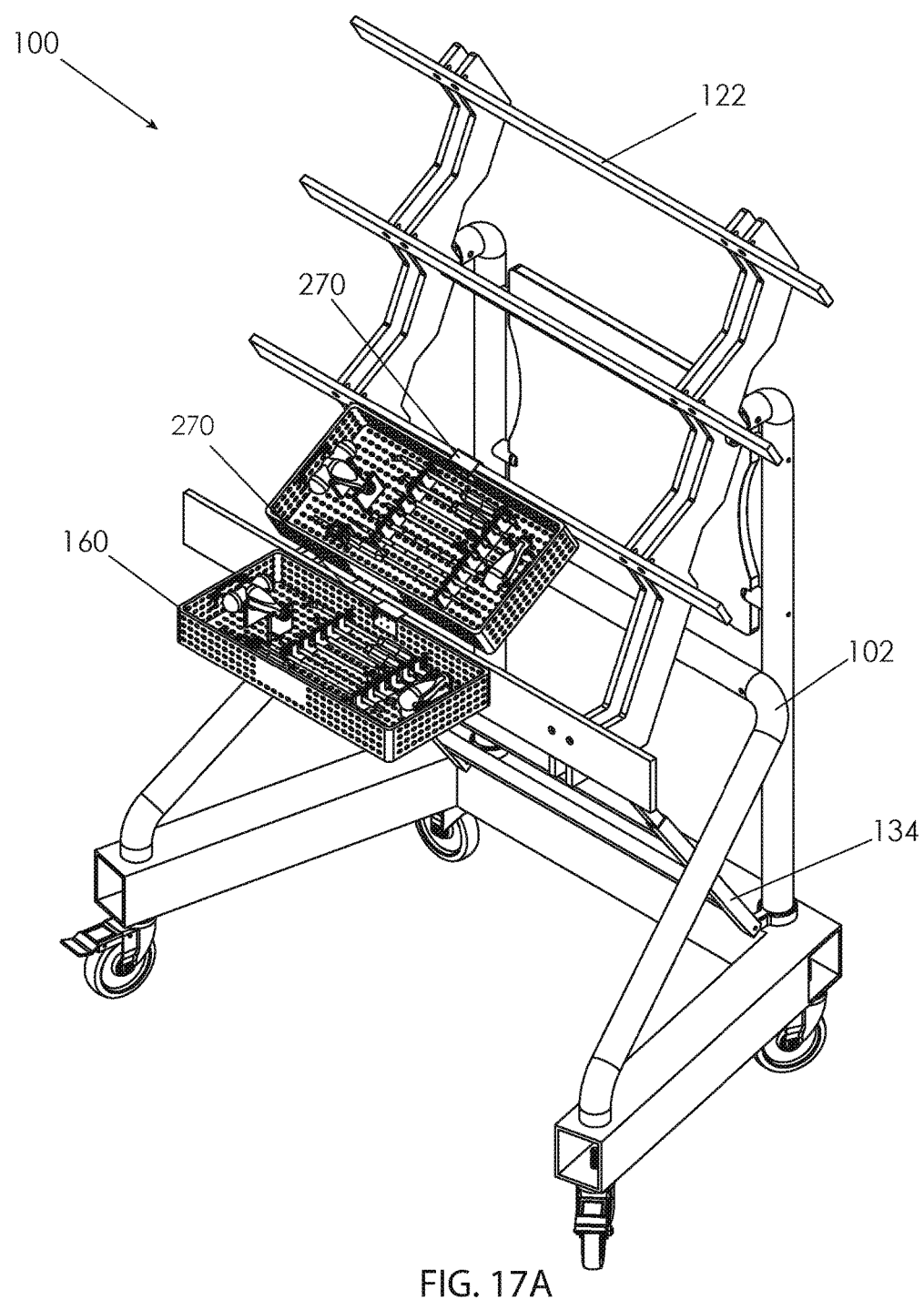
FIG. 17A is a perspective view of an embodiment of a rack according to the present disclosure with the instrument tray attachment device mounted on an instrument tray and attached to the rack.

As shown in FIG. 17A, the organizational rack system 100, has spine rail assembly 122 that rotates about the frame assembly 102 and is supported by the telescoping tube assembly 134 which is also mechanically connected to the frame assembly 102 and the instrument tray attachment assembly 270 which can be detachable attached to the instrument tray 160 so that it can be detachably attached to a spine rail assembly 122 without needing the tray shelf 150 (not pictured).

FIG. 17B shows the tray attachment assembly 270 removed from instrument tray 160 (not pictured). 17C shows an exploded view of tray attachment assembly 270. FIG. 17D shows a closed up view of the instrument tray attachment assembly 270 attached to instrument tray 160 so that the spine rail assembly 122 can maintain support of the instrument tray 160 without the need for the tray shelf 150 (not pictured).

Figure 18A:
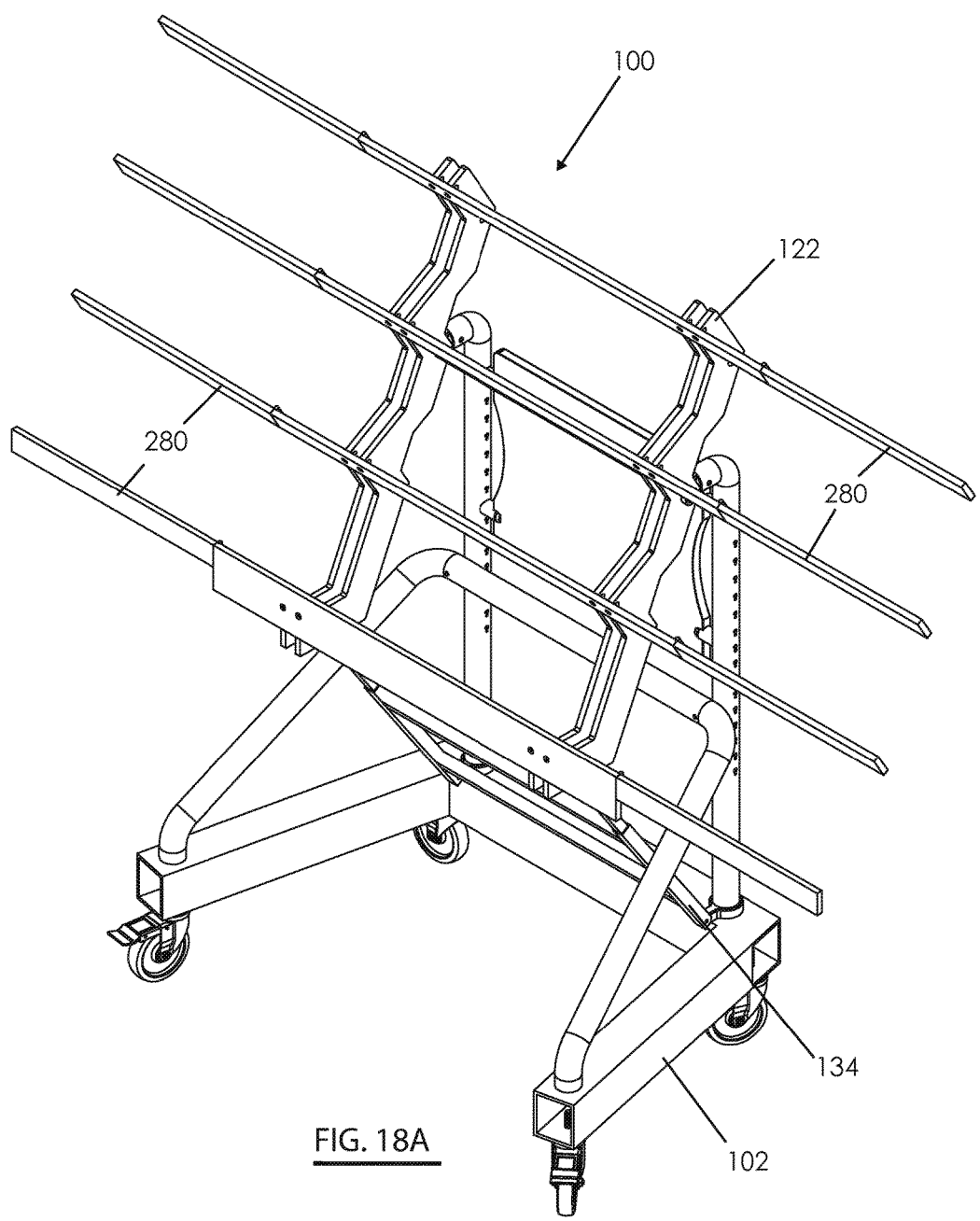
FIG. 18A is a perspective view of an embodiment of a rack according to the present disclosure with the tray shelves removed and the telescoping cross rails in an operational position.

As shown in FIG. 18A, the organizational rack system 100, has the spine rail assembly 122 that rotates about the frame assembly 102 and is supported by the telescoping tube assembly 134 which is also mechanically connected to the frame assembly 102 and the telescoping cross rail 280.

Figure 18B:
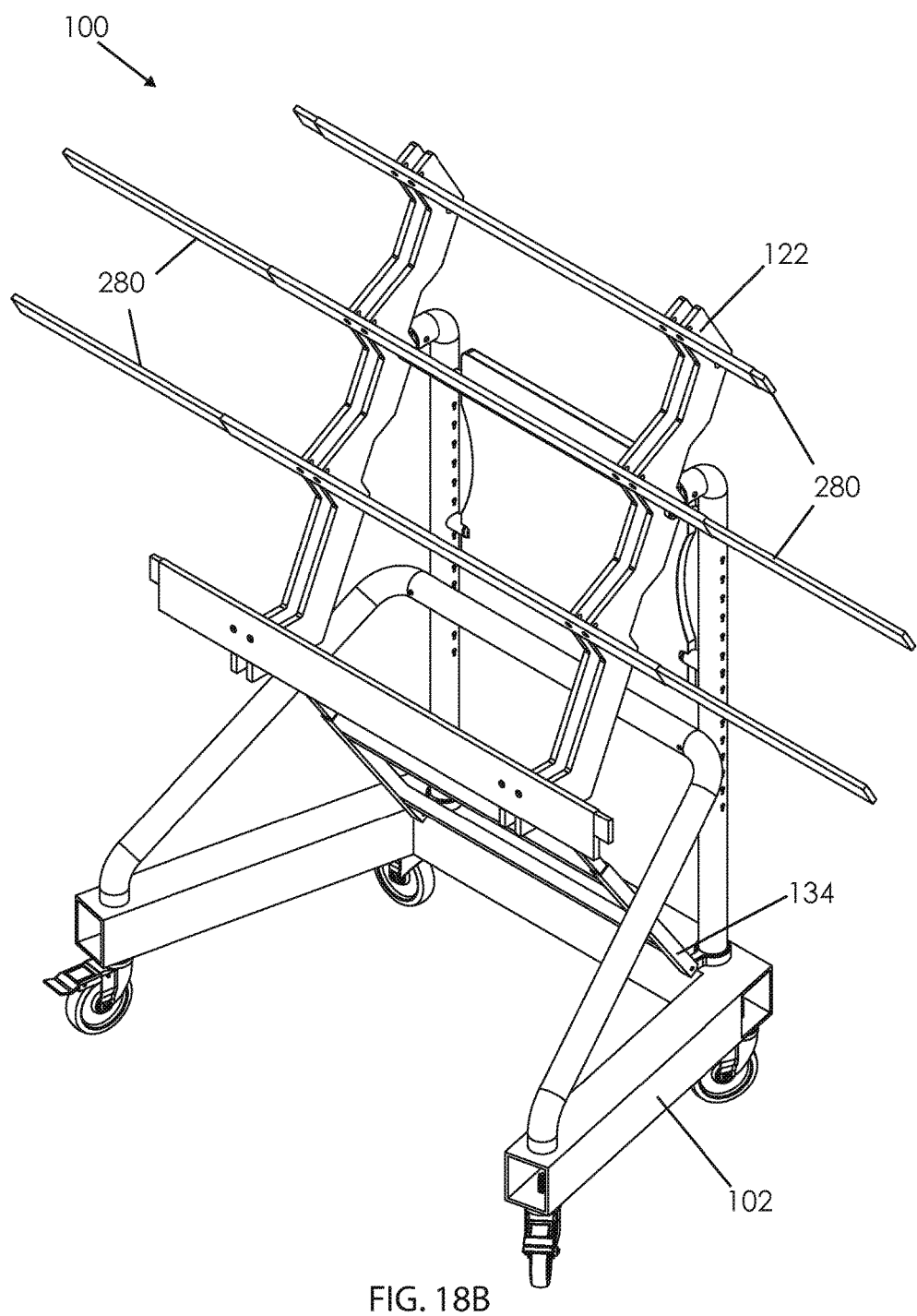
FIG. 18B is a perspective view of an embodiment of a rack according to the present disclosure with the tray shelves removed and the top and bottom telescoping cross rails in a storage position and the two middle telescoping cross rails in an operational position.

FIG. 18B shows different variations of the telescoping cross rail 280 two are collapsed and two are fully extended. The telescoping cross rail 280 can be adjusted from the collapsed position into the fully extended orientation by depressing the spring loaded pin 282 (not pictured).

Figure 18C:
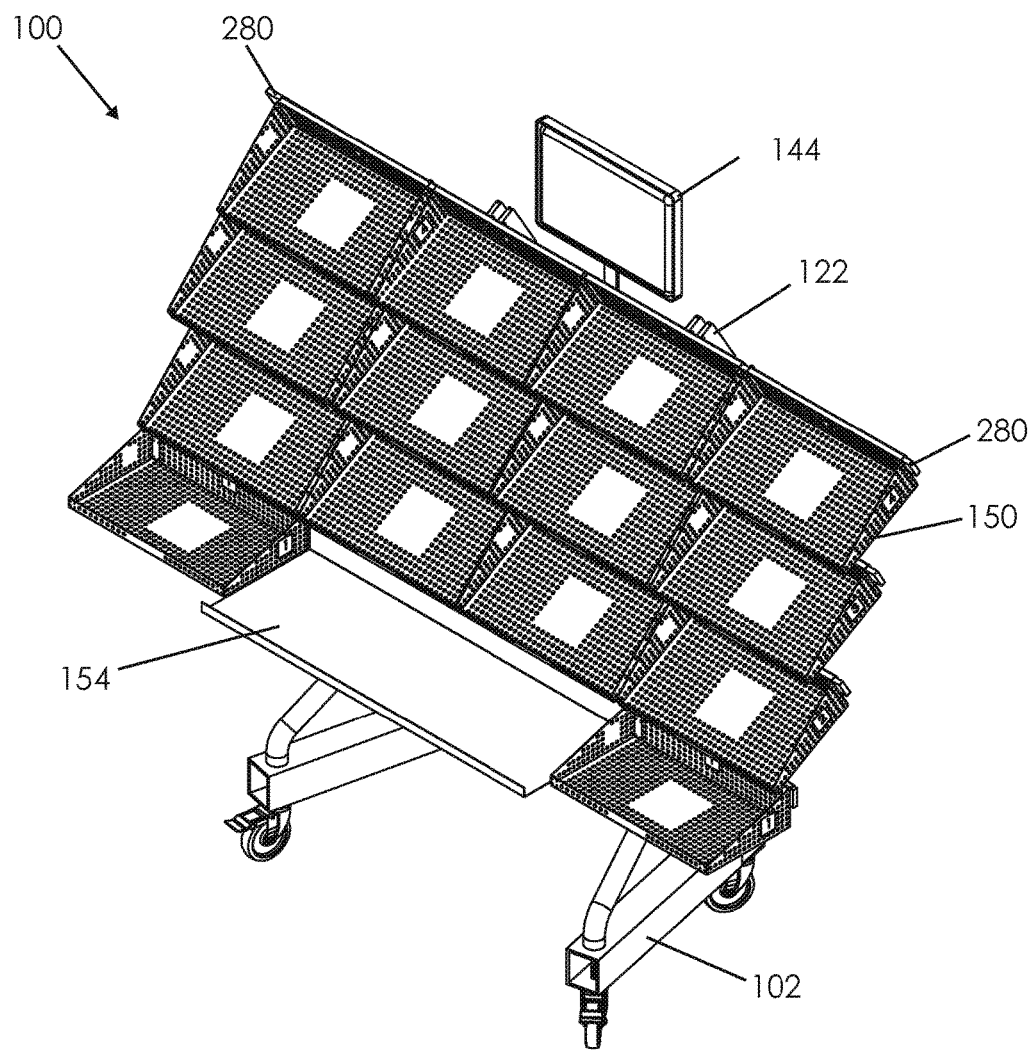
FIG. 18C is a perspective view of an embodiment of a rack according to the present disclosure with the telescoping cross rails, tray shelves, primary working table and interface assembly in an operational position.

As shown in FIG. 18C the telescoping cross rail 280 supports the tray shelf 150 along with the primary working shelf 154 while the frame assembly 102 supports the user interface assembly 144 in order to provide a visible and specific location the instrument tray 160 (not pictured).

Figure 19A:
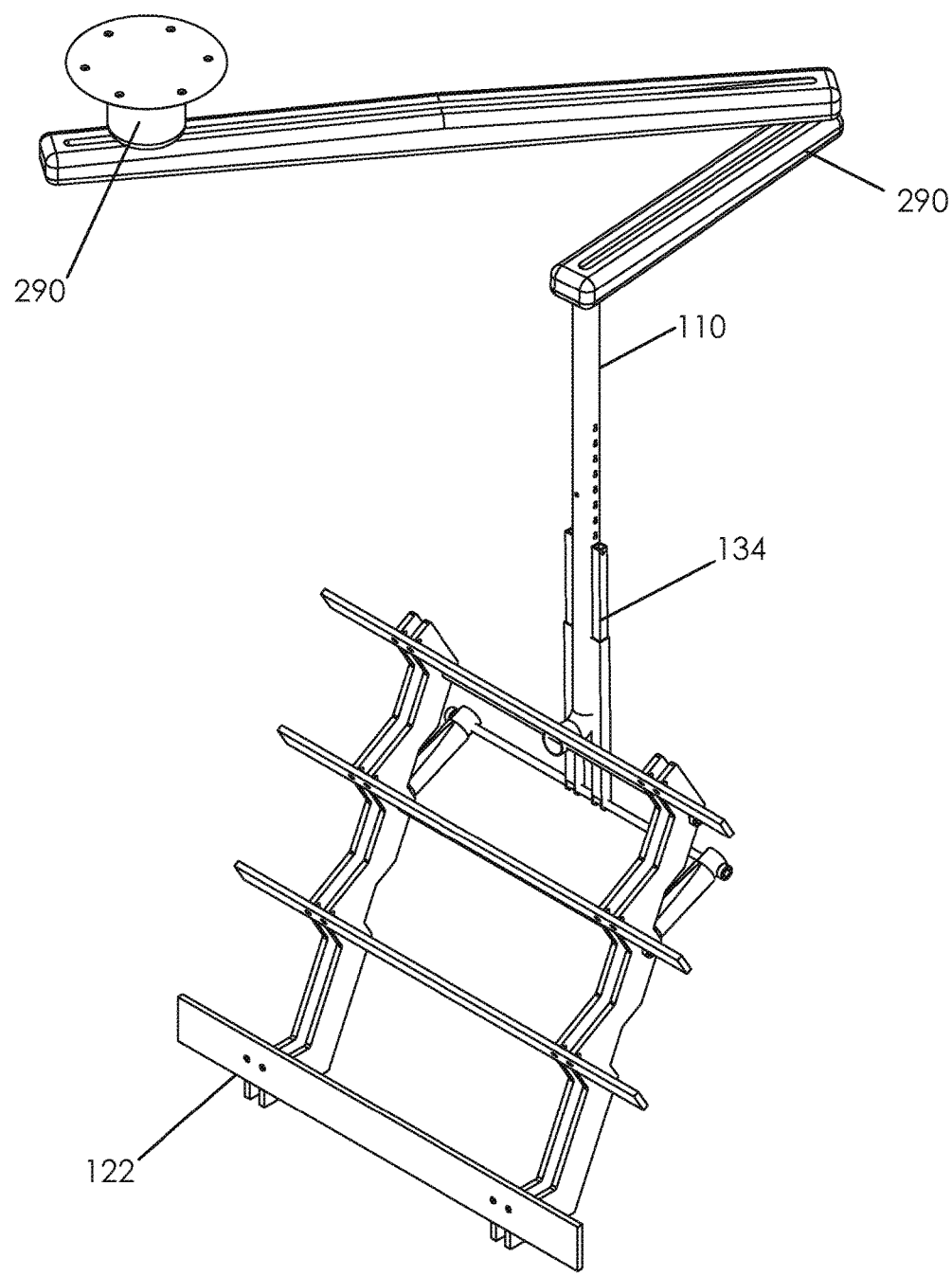
FIG. 19A is a perspective view of an embodiment of a rack according to the present disclosure with the frame assembly mounted on a ceiling boom with the tray shelves removed and rack in an operation position.

As shown in FIG. 19A the ceiling boom frame assembly 290 is mechanically connected the vertical support rail 110 which is mechanically connected to the telescoping tube assembly 134 which supports the spine rail assembly 122. The fully extended orientation of the telescoping tube assembly 134 maintains the correct in use position of the spine rail assembly 122.

Figure 19B:
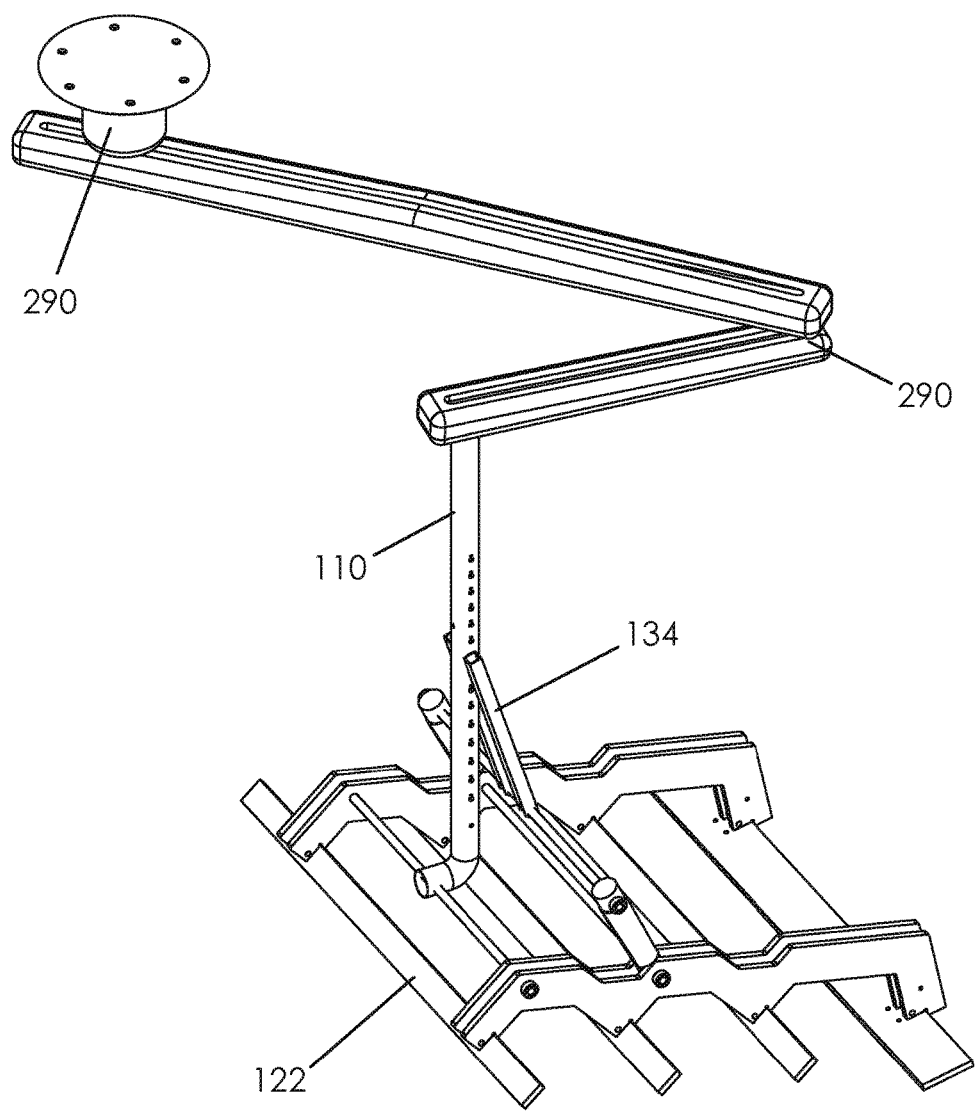
FIG. 19B is a perspective front view of an embodiment of a rack according to the present disclosure with the frame assembly mounted on a ceiling boom with the tray shelves removed and the rack in a storage position.
Figure 19C:
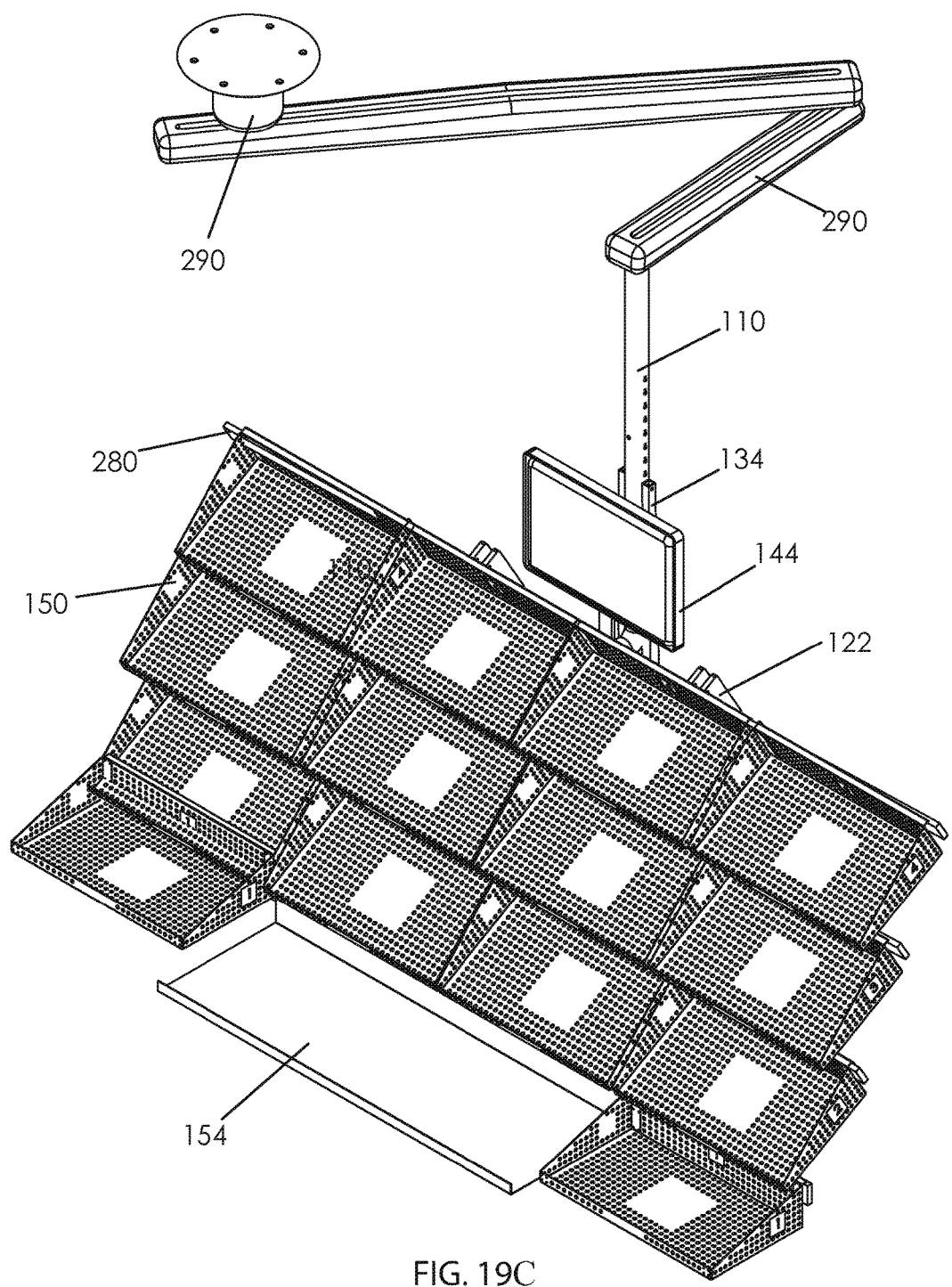
FIG. 19C is a perspective view of an embodiment of a rack according to the present disclosure with a ceiling mounted boom frame, tray shelves, primary working table and interface assembly in an operational position.

FIGS. 19B and 19 (show the ceiling boom frame assembly 290 mechanically connected the vertical support rail 110 which is mechanically connected to the telescoping tube assembly 134 which supports the spine rail assembly 122. The fully collapsed orientation of the telescoping tube assembly 134 maintains the storage position of the spine rail assembly 122.

Figure 20:
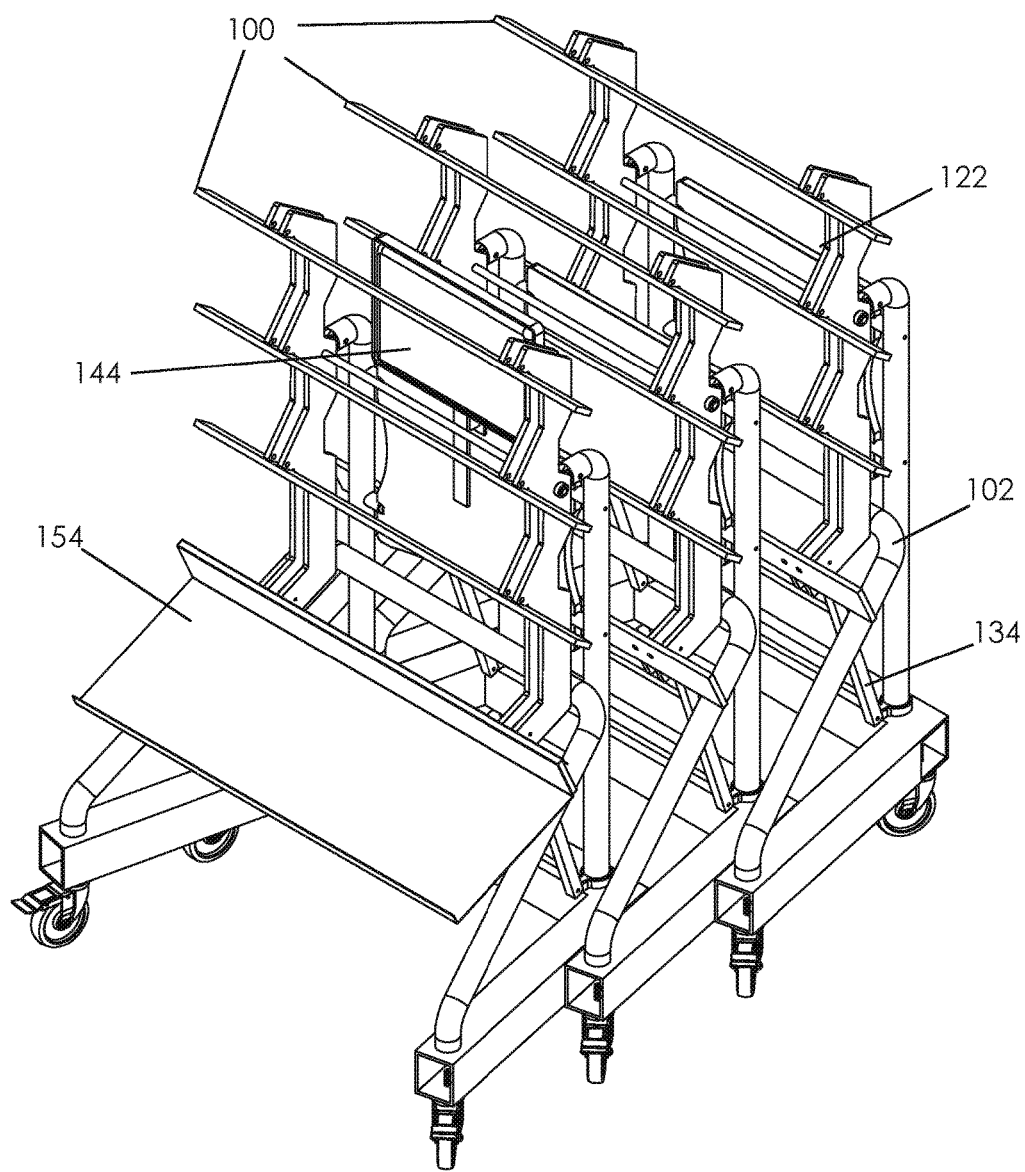
FIG. 20 is a perspective view of a first embodiment and a second embodiment of a rack according to the present disclosure in the storage position and nested together.

As shown in FIG. 20 the organization rack system 100 may be nested or stacked together with multiple organizational rack systems 100. The telescoping tube assembly 134 is fully collapsed so that the organization rack system 100 is in the storage position in order to reduce the surface area footprint from the organizational rack system 100.

Many variations on the basic design are possible. Some (not all) possible variations will now be quickly mentioned to help evoke the full scope of various aspects of the present disclosure. There may more or fewer than four cross rails on the spine assembly, the angle at which they are mounted to the spine may be greater or less than thirty degrees. The length of cross rails may be longer or shorter than forty two inches. The frame assembly may have fewer or more than two vertical wall rails. The frame assembly may be mounted and oriented on the ceiling. A variety of geometry may also exist for the rack assembly.

The invention claimed is:

1. An organizational rack system comprising:
   (a) a frame assembly having a base including non-parallel sides, a plurality of ground engaging wheels, and at least one vertical support rail mechanically attached to the base;
   (b) a tray shelf support assembly mechanically connected to the frame assembly, the tray shelf support assembly including a plurality of vertically-oriented multi-level shelf support panels,
   (c) a first tray shelf associated with a bottom level of at least one of the plurality of vertically-oriented multi-level shelf support panels at a first mounting angle; and
   (d) a second tray shelf associated with a second level of at least one of the plurality of vertically-oriented multi-level shelf support panels at a second mounting angle;
   (e) wherein the first mounting angle is different from the second mounting angle.

2. The organizational rack system of claim 1, further comprising a third tray shelf associated with a third level of at least one of the plurality of vertically-oriented multi-level shelf support panels at a third mounting angle.

3. The organizational rack system of claim 2, further comprising a fourth tray shelf associated with a fourth level of at least one of the plurality of vertically-oriented multi-level shelf support panels at a fourth mounting angle.

4. The organizational rack system of claim 3, wherein the second, third, and fourth mounting angles are the same.

5. The organizational rack system of claim 1, wherein the at least one tray shelf associated with the bottom level is parallel to the floor.

6. The organizational rack system of claim 3, wherein the mounting angle of at least one the second, third, and fourth tray shelves is thirty degrees.

7. The organizational rack system of claim 1, wherein the first tray shelf is configured to hold at least one instrument tray.

8. The organizational rack system of claim 1, further comprising a ceiling boom mechanically attached to the frame assembly.

9. The organizational rack system of claim 1, further comprising a user interface assembly that provides visible and specific location of an instrument tray.

10. The organizational rack system of claim 1, further comprising a light assembly attached to the frame assembly for providing extra light.

* * * * *